(12) United States Patent
Thatikonda et al.

(10) Patent No.: US 9,951,040 B2
(45) Date of Patent: Apr. 24, 2018

(54) 1,3,5-TRIAZINE BASED PI3K INHIBITORS AS ANTICANCER AGENTS AND A PROCESS FOR THE PREPARATION THEREOF

(71) Applicant: Council of Scientific and Industrial Research, New Delhi (IN)

(72) Inventors: Thanusha Thatikonda, Jammu (IN); Suresh Kumar, Jammu (IN); Umed Singh, Jammu (IN); Priya Mahajan, Jammu (IN); Girish Mahajan, Jammu (IN); Amit Nargotra, Jammu (IN); Fayaz Malik, Jammu (IN); Dilip Manikrao Mondhe, Jammu (IN); Ram Asrey Vishwakarma, Jammu (IN); Parvinder Pal Singh, Jammu (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 15/528,435

(22) PCT Filed: Nov. 17, 2015

(86) PCT No.: PCT/IN2015/050169
§ 371 (c)(1),
(2) Date: May 19, 2017

(87) PCT Pub. No.: WO2016/079760
PCT Pub. Date: May 26, 2016

(65) Prior Publication Data
US 2017/0342049 A1    Nov. 30, 2017

(30) Foreign Application Priority Data

Nov. 20, 2014  (IN) .......................... 3369/DEL/2014

(51) Int. Cl.
*C07D 401/04* (2006.01)
*C07D 401/14* (2006.01)
*A61K 31/53* (2006.01)
*A61K 31/5377* (2006.01)
*A61P 35/00* (2006.01)
*A61K 31/519* (2006.01)
*A61K 39/395* (2006.01)

(52) U.S. Cl.
CPC .......... *C07D 401/04* (2013.01); *A61K 31/519* (2013.01); *A61K 31/53* (2013.01); *C07D 401/14* (2013.01); *A61K 39/39558* (2013.01); *A61K 2300/00* (2013.01)

(58) Field of Classification Search
CPC .. C07D 413/04; C07D 413/14; C07D 401/14; C07D 403/14; A61K 31/53; A61K 31/5377
USPC ......................................... 544/113; 514/231.5
See application file for complete search history.

(56) References Cited

FOREIGN PATENT DOCUMENTS

| EP | 1864665 A1 | 12/2007 |
|---|---|---|
| WO | WO-2008/032064 A1 | 3/2008 |
| WO | WO-2009/066084 A1 | 5/2009 |
| WO | WO-2010/110685 A2 | 9/2010 |
| WO | WO-2011/135520 A1 | 11/2011 |

OTHER PUBLICATIONS

International Patent Application No. PCT/IN2015/050169, Search Report and Written Opinion dated Mar. 24, 2016, 12 pgs.

*Primary Examiner* — Vankataraman Balasubramanian
(74) *Attorney, Agent, or Firm* — Schwegman Lundberg & Woessner, P.A.

(57) ABSTRACT

The present invention describes heterocyclic compounds of general Formula 1 and their method of preparation thereof. The present invention describes general Formula 1 which inhibits phosphoinositide 3-kinase (PI3K) and can be used as the anticancer agents.

(I)

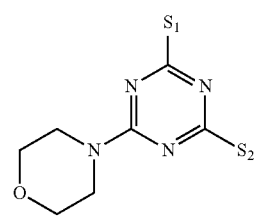

8 Claims, 5 Drawing Sheets

Scheme 1: Reagents and conditions: a) DCM, -50 °C, 2h; b) DMF, -5 °C , anhy K₂CO₃; c) DMF, rt, K₂CO₃

Fig 2

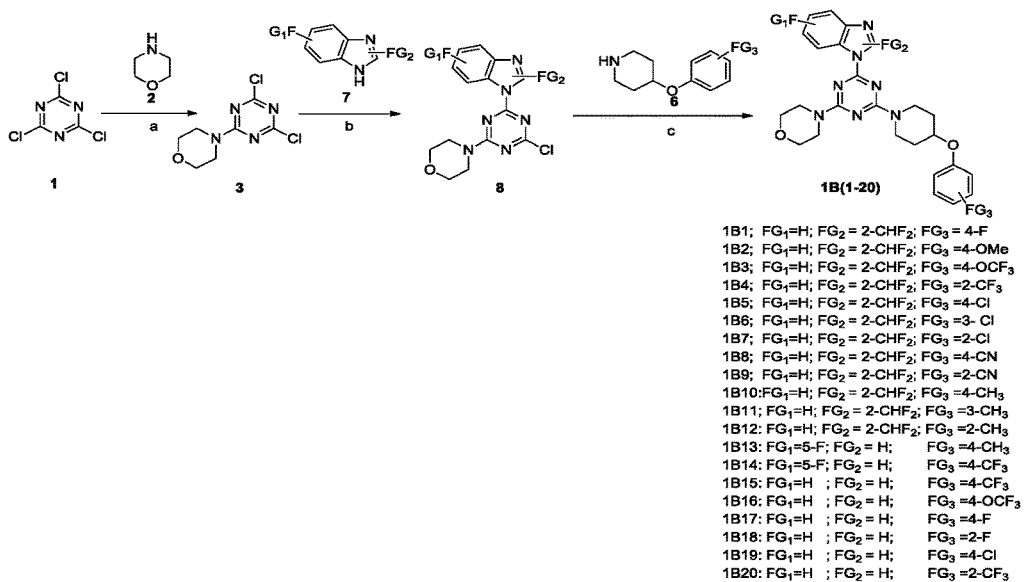

1B1; FG₁=H; FG₂ = 2-CHF₂; FG₃ = 4-F
1B2; FG₁=H; FG₂ = 2-CHF₂; FG₃ =4-OMe
1B3; FG₁=H; FG₂ = 2-CHF₂; FG₃ =4-OCF₃
1B4; FG₁=H; FG₂ = 2-CHF₂; FG₃ =2-CF₃
1B5; FG₁=H; FG₂ = 2-CHF₂; FG₃ =4-Cl
1B6; FG₁=H; FG₂ = 2-CHF₂; FG₃ =3- Cl
1B7; FG₁=H; FG₂ = 2-CHF₂; FG₃ =2-Cl
1B8; FG₁=H; FG₂ = 2-CHF₂; FG₃ =4-CN
1B9; FG₁=H; FG₂ = 2-CHF₂; FG₃ =2-CN
1B10:FG₁=H; FG₂ = 2-CHF₂; FG₃ =4-CH₃
1B11; FG₁=H; FG₂ = 2-CHF₂; FG₃ =3-CH₃
1B12: FG₁=H; FG₂ = 2-CHF₂; FG₃ =2-CH₃
1B13: FG₁=5-F; FG₂ = H;    FG₃ =4-CH₃
1B14: FG₁=5-F; FG₂ = H;    FG₃ =4-CF₃
1B15: FG₁=H  ; FG₂ = H;    FG₃ =4-CF₃
1B16: FG₁=H  ; FG₂ = H;    FG₃ =4-OCF₃
1B17: FG₁=H  ; FG₂ = H;    FG₃ =4-F
1B18: FG₁=H  ; FG₂ = H;    FG₃ =2-F
1B19: FG₁=H  ; FG₂ = H;    FG₃ =4-Cl
1B20: FG₁=H  ; FG₂ = H;    FG₃ =2-CF₃

Scheme 2: Reagents and conditions:  a) DCM, -50 °C, 2h; b) DMF, -5 °C , anhy K₂CO₃; c) DMF, rt, K₂CO₃

Fig 3

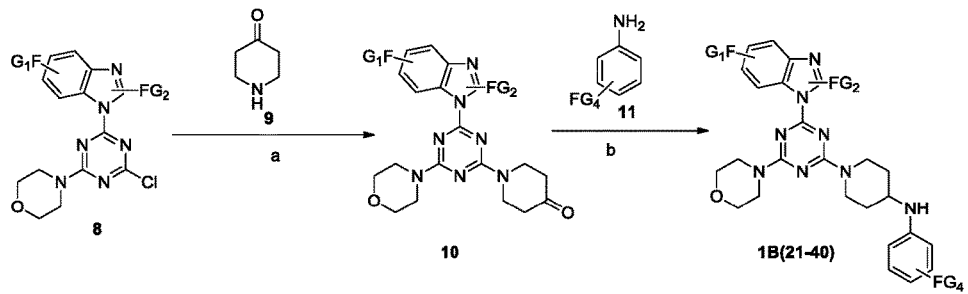

1B21; FG$_1$=H; FG$_2$ = 2-CHF$_2$; FG$_4$ = 4-F
1B22; FG$_1$=H; FG$_2$ = 2-CHF$_2$; FG$_4$ =4-CF3
1B23; FG$_1$=H; FG$_2$ = 2-CHF$_2$; FG$_4$ =4-OCF$_3$
1B24; FG$_1$=H; FG$_2$ = 2-CHF$_2$; FG$_4$ =4-OCH3
1B25; FG$_1$=H; FG$_2$ = 2-CHF$_2$; FG$_4$ =4-Br
1B26; FG$_1$=H; FG$_2$ = 2-CHF$_2$; FG$_4$ =3,4-di Cl
1B27; FG$_1$=H; FG$_2$ = 2-CHF$_2$; FG$_4$ =2-F
1B28; FG$_1$=H; FG$_2$ = 2-CHF$_2$; FG$_4$ =2-OCH3
1B29; FG$_1$=H; FG$_2$ = 2-CHF$_2$; FG$_4$ =2-CF3
1B30:FG$_1$=H; FG$_2$ = 2-CHF$_2$; FG$_4$ =4-CH$_3$
1B31; FG$_1$=H; FG$_2$ = 2-CHF$_2$; FG$_4$ =3-OCH$_3$
1B32: FG$_1$=H; FG$_2$ = 2-CHF$_2$; FG$_4$ =2-CH$_3$
1B33: FG$_1$=5-F; FG$_2$ = H;   FG$_4$ =4-CH$_3$
1B34: FG$_1$=5-F; FG$_2$ = H;   FG$_4$ =4-CF$_3$
1B35: FG$_1$=H ; FG$_2$ = H;    FG$_4$ =4-CF$_3$
1B36: FG$_1$=H ; FG$_2$ = H;    FG$_4$ =4-OCF$_3$
1B37: FG$_1$=H ; FG$_2$ = H;    FG$_4$ =4-F
1B38: FG$_1$=H ; FG$_2$ = H;    FG$_4$ =2-F
1B39: FG$_1$=H ; FG$_2$ = H;    FG$_4$=4-Cl
1B40: FG$_1$=H ; FG$_2$ = H;    FG$_4$ =2-CF3

Scheme 3: Reagents and conditions: (a) DMF, K$_2$CO$_3$ , rt, 24h (b) CH$_3$COOH, Na(OAC)$_3$BH, 24h, rt Scheme 4: Reagents and conditions: (a) DCM, Et$_3$N, Cu(OAC)$_2$, 12h, rt 1B46: FG$_1$=H; FG$_2$ = 2-CHF$_2$; FG$_4$ = 4-F
1B47: FG$_1$=H; FG$_2$ = 2-CHF$_2$; FG$_4$ =4-OMe
1B48: FG$_1$=H; FG$_2$ = 2-CHF$_2$; FG$_4$ =4-OCF$_3$
1B49: FG$_1$=H; FG$_2$ = 2-CHF$_2$; FG$_4$ =4-CF$_3$
1B50: FG$_1$=H; FG$_2$ = 2-CHF$_2$; FG$_4$ =4-Cl Scheme 5: Reagents and conditions: a) DCM, -50 °C, 2h; b) DMF, -5 °C, anhy K$_2$CO$_3$; c) DMF, rt, K$_2$CO$_3$ (d) Na(OAC)$_3$BH, CH$_3$COOH, DCM, 24h, rt

1,3,5-TRIAZINE BASED PI3K INHIBITORS AS ANTICANCER AGENTS AND A PROCESS FOR THE PREPARATION THEREOF

CLAIM OF PRIORITY

This application is a U.S. National Stage Filing under 35 U.S.C. 371 from International Application No. PCT/IN2015/050169, filed on Nov. 17, 2015, and published as WO 2016/079760 A1 on May 26, 2016, which claims the benefit of priority to Indian Patent Application No. 3369/DEL/2014, filed on Nov. 20, 2014, each of which is hereby incorporated by reference herein in its entirety.

FIELD OF THE INVENTION

The present invention relates to novel 1,3,5-substituted triazine containing heterocyclic compounds of general formula 1, which inhibits phosphoinositide 3-kinase (PI3K). The invention also relates to their method of preparation and their use as an agents or drugs for cancer therapy.

BACKGROUND AND PRIOR ART OF THE INVENTION

At cellular level, phosphoinositide-3-kinase (PI3K) signalling contributes to many important processes, such as cell cycle progression, cell growth, survival and migration and intracellular vesicular transport. The PI3K represents the family of lipid kinases that can be classified into three subfamilies according to structure and substrate specificity viz., class I, class II and class III (Liu et al., Nature review drug discovery, 2009, 8, 627; Courteny et al., J Clin Oncol, 2010, 28, 1075). The class I PI3Ks are the most extensively studied among lipid kinases, are heterodimeric proteins; each containing a smaller regulatory domain and a larger 110 kDa catalytic domain, which occur in four isoforms differentiated as p110α, p110β, p110γ, and p110δ (Walker et al., Mol. Cell 2000, 6, 909). Moreover, Isoform selective inhibitors capable of attenuating PI3K signalling should have significant therapeutic potential for the treatment of cancer, inflammatory (Barber et al., Nat. Med. 2005, 11, 933), cardiovascular diseases and autoimmune disorders. In cancer, evidence suggests that inhibition of the class 1A PI3 kinase p110α appear to be the most appropriate to target, as in number of cancer, p110α isoform is amplified and activated (Stephens et al., Curr. Opin. Pharmacol. 2005, 5, 357).

In the last decade, many small molecules have been discovered as PI3K isoform inhibitors and presenting the new opportunities as therapeutic agents. Some of the small molecules are presently in either phase I or II clinical trial against different type of cancers. Examples includes NVP-BEZ235 developed by Novartis, (Garcia-Echeverria et al., WO2006/122806A2), NVP-BGT226 developed by Novartis, (Kwang et al., Clin cancer res. 2011, 17(22), 7114), XL-147, XL-765 developed by Exelixis, (P. Wu et al., Eur. J. Med. Chem. 2011, 46, 5540), GDC0941 developed by Genentech, (Adrian et al., J. Med. Chem. 2008, 51, 5522), PKI-587 developed by Pfizer, (Mallon et al., Clin cancer res. 2011, 17(10), 3194), GSK1059615 developed by GSK, (Steven D. Knight et al., ACS Med. Chem. Lett. 2010, 1, 39), ZSTK474 developed by Zenyaku kogyo, (Yaguchi et al., J. Natl. Cancer inst. 2006, 98, 545; Kong et al., Cancer sci. 2007, 98, 1439; Gordon et al., J. Med. Chem. 2011, 54, 7105-7126; Gordon et al., WO2010/110686A1; Vladimir et al., WO2011/135520A1; Gordon et al., WO2010/110685A2; Venkatesan et al., WO2009/143317A1) etc. In spite of having many PI3K inhibitors in pre-clinical and different clinical trials, still there is need for the discovery of new PI3K inhibitors for the treatment of cancer.

OBJECTIVE OF THE INVENTION

The main object of the present invention is to provide 1,3,5-substituted triazine containing heterocyclic compounds as anti-cancer agents. Still another object of the present invention is to provide a process for the preparation of novel 1,3,5-substituted based compounds. Yet another object of the present invention is to provide the therapy for the treatment of cancer

SUMMARY OF THE INVENTION

The present invention relates to 1,3,5-substituted triazine containing heterocyclic compounds, their method of preparation and their use as drugs for treating cancer.

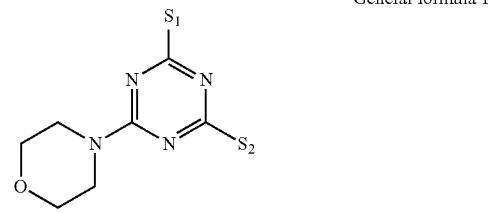

General formula 1

In a first aspect, the present invention pertains to a compound having a general formula 1:

Wherein substituent '$S_1$' is selected from one of the formula Ia or Ib

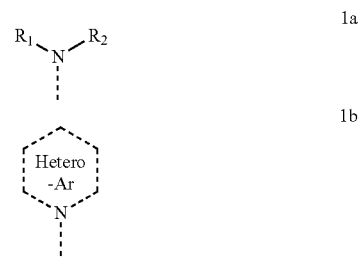

and substituent '$S_2$' selected from the group consisting of 1c

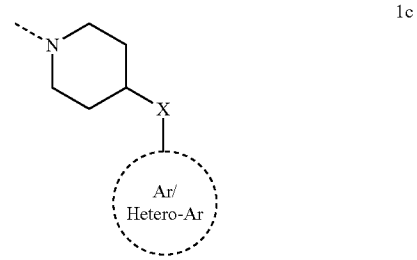

'X' is independently selected from any of $NR_3$, O, $CH_2$,

'$R_1$, $R_2$,' are independently selected from any of un/substituted alkyl $C_1$-$C_{14}$, un/substituted acyl $C_2$ to $C_{14}$, un/substituted phenyl ring and further substitution contains any of the following atoms or groups such as F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl etc either mono or di or poly at any of the available position $R_3$ is independently selected from any of H, un/substituted alkyl $C_1$-$C_{14}$, un/substituted acyl $C_2$ to $C_{14}$, un/substituted phenyl ring and further substitution contains any of the following atoms or groups such as F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl etc either mono or di or poly at any of the available position

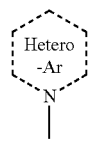

is independently selected from any of following un/substituted N-heterocycles such as indolyl, triazolyl, pyrrolyl, imidazoyl, benzotriazolyl, benzoimidazolyl, thiazoyl etc attached though N-atom or any of the available ring position and further substituted heterocycles contains any of the following atom or group such as F, Cl, Br, I, CN, $NR_4R_5$, $CF_3$, $CHF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl 'Ar' is independently selected from any of un/substituted phenyl, un/substituted napthyl and attached through any of the available ring position and further substitution selected from any of the following atom or group such as F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl 'Hetero-Ar' is independently selected from any of un/substituted heterocycles such as pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl, indolyl, benzotriazolyl, benzoimidazolyl etc and attached through any of the available ring position and further substituted heterocycles contains any of the following atom or group such as F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl $R_4$, $R_5$, $R_6$, $R_7$, $R_8$, $R_9$, $R_{10}$, $R_{11}$, $R_{12}$, $R_{13}$, $R_{14}$, $R_{15}$, $R_{14}$ and $R_{17}$' are independently selected from any of following substitution such as H, linear alkyl chain $C_1$-$C_{10}$, branched alkyl chain $C_3$-$C_{10}$, un/substituted phenyl ring.

In another aspect, a preferred subclass have following formulas 1A or 1B belong to general formula 1

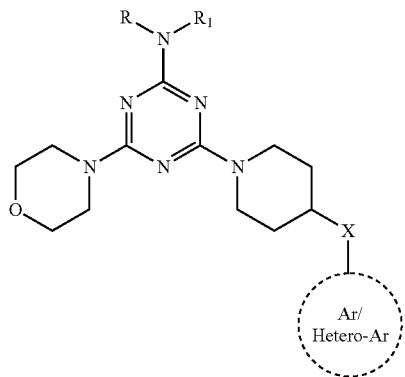

1A

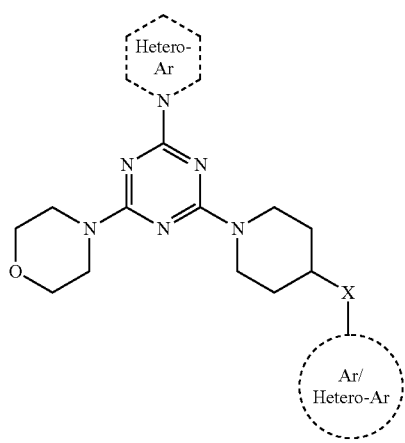

1B

'X' is independently selected from any of $NR_3$, O, $CH_2$,

'$R_1$, $R_2$,' are independently selected from any of following atom or groups un/substituted alkyl $C_1$-$C_{14}$, un/substituted acyl $C_2$ to $C_{14}$, un/substituted phenyl ring, un/substituted heterocycles and further substitution contains any of the following atoms or groups such as F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl etc either mono or di or poly substituted at any of the available position $R_3$ is independently selected from any of H, un/substituted alkyl $C_1$-$C_{14}$, un/substituted acyl $C_2$ to $C_{14}$, un/substituted phenyl ring and further substitution contains any of the following atoms or groups such as F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl either mono or di or poly at any of the available position

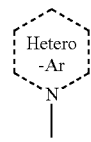

is independently selected from any of following un/substituted N-heterocycles such as indolyl, triazolyl, pyrrolyl, imidazoyl, benzotriazolyl, benzoimidazolyl, thiazoyl etc attached though N-atom or any of the available ring position and further substituted heterocycles contains any of the following atom or group such as F, Cl, Br, I, CN, $NR_4R_5$, $CF_3$, $CHF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl, 'Ar' is independently selected from any of un/substituted phenyl, un/substituted napthyl etc and attached through any of the available ring position and further substitution selected from any of the following atom or group such as F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl, 'Hetero-Ar' is independently selected from any of un/substituted heterocycles such as pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl, indolyl, benzotriazolyl, benzoimidazolyl etc and attached through any of the available ring position and further substituted heterocycles contains any of the following atom or group such as F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl, $R_4$, $R_5$, $R_6$, $R_7$, $R_8$, $R_9$, $R_{10}$, $R_{11}$, $R_{12}$, $R_{13}$, $R_{14}$, $R_{15}$, $R_{14}$ and $R_{17}'$ are independently selected from any of following substitution such as H, linear alkyl chain $C_1$-$C_{10}$, branched alkyl chain $C_3$-$C_{10}$, un/substituted phenyl ring.

In yet another embodiment of the present invention, the compounds of general formula 1 are useful as PI3K anticancer agent.

In still another embodiment of the present invention, the compounds of general formula 1 inhibit PI3Kα isoform.

In yet another embodiment of the present invention, the compounds of general formula 1 exhibit an in vitro cancer cell line activity.

In another embodiment of the present invention, a process for the preparation of the compounds of general formula 1 comprising of following steps:
(i) reacting disubstituted triazine compound of formula 5 or 8 with aryloxy piperidines or piperidones in an organic solvent selected from a group consisting of DMF, THF, $CH_3CN$ (added) in the presence of alkali metal carbonate selected from a group consisting of $K_2CO_3$, $Na_2CO_3$, $Cs_2CO_3$ (added) at a temperature ranging between 10° C. to 80° C. for a period ranging between 1 to 24 hrs, to obtain compound of formula 1A(1-20) or 1B(1-20) or trisubstituted triazine compound 10 or 15,
(ii) reacting trisubstituted triazine compound 10 or 15 with substituted aryl amine of formula 11, wherein FG4 is selected from a group consisting of 4F, 4-$CF_3$, 4-$OCH_3$, 4-Br, 3, 4 DiCl, 2-F, 2-$OCH_3$, 2-$CF_3$, 3-$OCH_3$, 2-$CH_3$, 4-$CH_3$ (added) in an organic solvent selected from a group consisting of DCM, DCE, THF, MeOH (added) in presence of acetic acid and a reducing agent selected from a group consisting of sodium triacetoxy borohydride, sodium borohydride (added) at a temperature ranging between 10° C. to 80° C. for a period ranging between 1 to 24 hrs, to obtain compound 1B (21-40) or 1B (46-50) respectively,
(iii) reacting trisubstituted triazine compound 1B21 with substituted aryl boronic acid of formula 12, wherein FG5 is selected from a group consisting of halogen or $CF_3$, in an organic solvent selected from a group consisting of DCM, DCE, MeOH, $CH_3CN$ (added) in presence of triethylamine and copper acetate at a temperature ranging between 10° C. to 80° C. for a period in the range of 1 to 24 hrs, to obtain compound of formula 1B(41-45).

BRIEF DESCRIPTION OF THE DRAWINGS

FIG. 2 shows the synthetic approach (scheme2) for the synthesis of compounds 1B (1-20).
FIG. 3 shows the synthetic approach (scheme3) for the synthesis of compounds 1B (21-40).

DETAILED DESCRIPTION OF THE INVENTION

Figure 1:
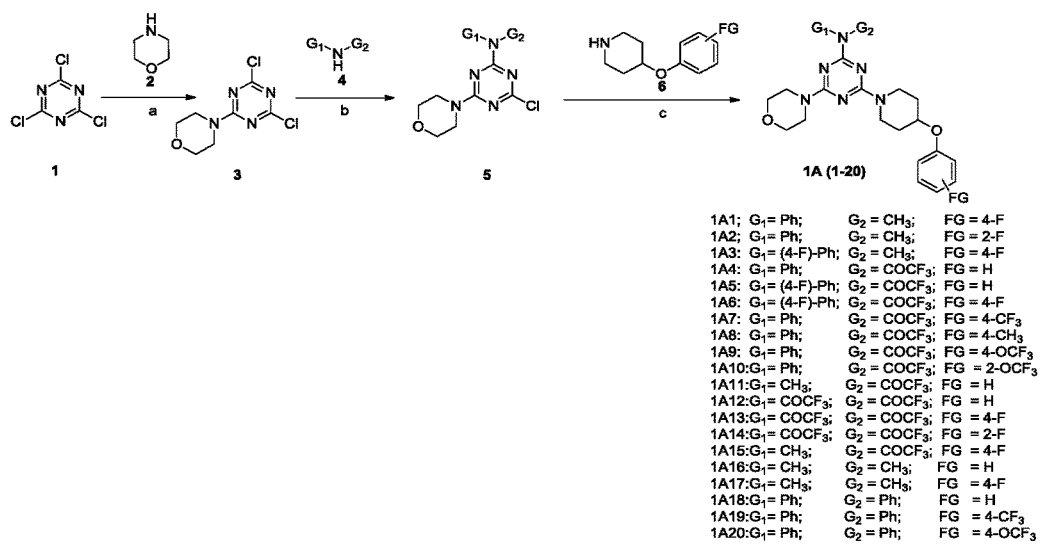
FIG. 1 shows the synthetic approach (scheme1) for the synthesis of compounds 1A (1-20).

The present invention relates to newer generation of triazine based compounds, their method of preparation and to their use as drugs for treating cancer.

General formula 1

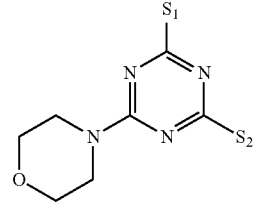

In a first aspect, the present invention pertains to a compound having a general formula 1:

Wherein substituent 'S₁' is selected from one of the formula Ia or Ib

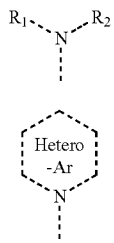

1a

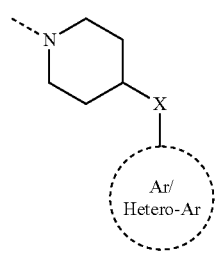

1b and substituent 'S₂' selected from the group consisting of 1c

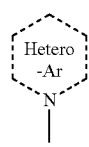

1c

'X' is independently selected from any of NR$_3$, O, CH$_2$,

'R$_1$, R$_2$' are independently selected from any of un/substituted alkyl C$_1$-C$_{14}$, un/substituted acyl C$_2$ to C$_{14}$, un/substituted phenyl ring and further substitution contains any of the following atoms or groups such as F, Cl, Br, I, CN, NR$_4$R$_5$, CF$_3$, CHCF$_2$, CH$_2$F, OCF$_3$, OCH$_2$CF$_3$, OR$_6$, NO$_2$, NO, CHR$_7$R$_8$, alkyl chain from C$_1$ to C$_{14}$, COOR$_9$, CHO, COR$_{10}$, COCF$_3$, COCH$_2$CF$_3$, SR$_{11}$, SOR$_{12}$, SO$_2$R$_{13}$, SONR$_{14}$R$_{15}$, SO$_2$NR$_{14}$R$_{17}$, cycloalkyl etc either mono or di or poly at any of the available position R$_3$ is independently selected from any of H, un/substituted alkyl C$_1$-C$_{14}$, un/substituted acyl C$_2$ to C$_{14}$, un/substituted phenyl ring and further substitution contains any of the following atoms or groups such as F, Cl, Br, I, CN, NR$_4$R$_5$, CF$_3$, CHCF$_2$, CH$_2$F, OCF$_3$, OCH$_2$CF$_3$, OR$_6$, NO$_2$, NO, CHR$_7$R$_8$, alkyl chain from C1 to C14, COOR$_9$, CHO, COR$_{10}$, COCF$_3$, COCH$_2$CF$_3$, SR$_{11}$, SOR$_{12}$, SO$_2$R$_{13}$, SONR$_{14}$R$_{15}$, SO$_2$NR$_{14}$R$_{17}$, cycloalkyl etc either mono or di or poly at any of the available position is independently selected from any of following un/substituted N-heterocycles such as indolyl, triazolyl, pyrrolyl, imidazoyl, benzotriazolyl, benzoimidazolyl, thiazoyl etc attached though N-atom or any of the available ring position and further substituted heterocycles contains any of the following atom or group such as F, Cl, Br, I, CN, NR$_4$R$_5$, CF$_3$, CHF$_2$, CH$_2$F, OCF$_3$, OCH$_2$CF$_3$, OR$_6$, NO$_2$, NO, CHR$_7$R$_8$, alkyl chain from C$_1$ to C$_{14}$, COOR$_9$, CHO, COR$_{10}$, COCF$_3$, COCH$_2$CF$_3$, SR$_{11}$, SOR$_{12}$, SO$_2$R$_{13}$, SONR$_{14}$R$_{15}$, SO$_2$NR$_{14}$R$_{17}$, cycloalkyl, 'Ar' is independently selected from any of un/substituted phenyl, un/substituted napthyl etc and attached through any of the available ring position and further substitution selected from any of the following atom or group such as F, Cl, Br, I, CN, NR$_4$R$_5$, CF$_3$, CHCF$_2$, CH$_2$F, OCF$_3$, OCH$_2$CF$_3$, OR$_6$, NO$_2$, NO, CHR$_7$R$_8$, alkyl chain from C$_1$ to C$_{14}$, COOR$_9$, CHO, COR$_{10}$, COCF$_3$, COCH$_2$CF$_3$, SR$_{11}$, SOR$_{12}$, SO$_2$R$_{13}$, SONR$_{14}$R$_{15}$, SO$_2$NR$_{14}$R$_{17}$, cycloalkyl, 'Hetero-Ar' is independently selected from any of un/substituted heterocycles such as pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl, indolyl, benzotriazolyl, benzoimidazolyl etc and attached through any of the available ring position and further substituted heterocycles contains any of the following atom or group such as F, Cl, Br, I, CN, NR$_4$R$_5$, CF$_3$, CHCF$_2$, CH$_2$F, OCF$_3$, OCH$_2$CF$_3$, OR$_6$, NO$_2$, NO, CHR$_7$R$_8$, alkyl chain from C$_1$ to C$_{14}$, COOR$_9$, CHO, COR$_{10}$, COCF$_3$, COCH$_2$CF$_3$, SR$_{11}$, SOR$_{12}$, SONR$_{14}$R$_{15}$, SO$_2$NR$_{14}$R$_{17}$, cycloalkyl, R$_4$, R$_5$, R$_6$, R$_7$, R$_8$, R$_9$, R$_{10}$, R$_{11}$, R$_{12}$, R$_{13}$, R$_{14}$, R$_{15}$, R$_{14}$ and R$_{17}$' are independently selected from any of following substitution such as H, linear alkyl chain C$_1$-C$_{10}$, branched alkyl chain C$_3$-C$_{10}$, un/substituted phenyl ring.

In another aspect, a preferred subclass have following formulas 1A or 1B belong to general formula 1

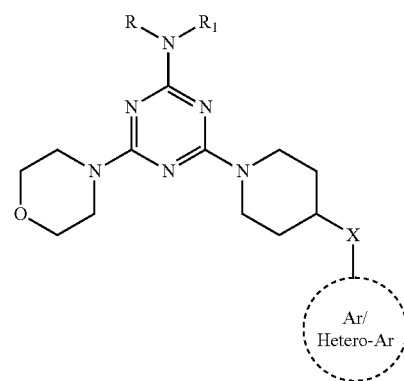

1A

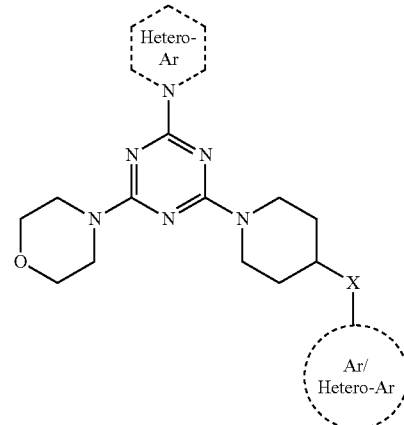

1B

'X' is independently selected from any of NR$_3$, O, CH$_2$,

'R$_1$, R$_2$' are independently selected from any of following atom or groups un/substituted alkyl C$_1$-C$_{14}$, un/substituted acyl C$_2$ to C$_{14}$, un/substituted phenyl ring, un/substituted heterocycles and further substitution contains any of the following atoms or groups such as F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl etc either mono or di or poly substituted at any of the available position $R_3$ is independently selected from any of following atom or groups H, un/substituted alkyl $C_1$-$C_{14}$, un/substituted acyl $C_2$ to $C_{14}$, un/substituted phenyl ring, un/substituted heterocycles and further substitution contains any of the following atoms or groups such as F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{ii}$, $SOR_{12}$, $SO_2R_{13}$, $SONR_{14}R_{15}$, $SO_2NR_{14}R_{17}$, cycloalkyl etc either mono or di or poly substituted at any of the available position

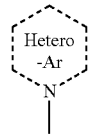

is independently selected from any of following un/substituted N-heterocycles such as indolyl, triazolyl, pyrrolyl, imidazoyl, benzotriazolyl, benzoimidazolyl, thiazoyl etc attached though N-atom or any of the available ring position and further substituted heterocycles contains any of the following atom or group such as F, Cl, Br, I, CN, $NR_4R_5$, $CF_3$, $CHF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl, 'Ar' is independently selected from any of un/substituted phenyl, un/substituted napthyl etc and attached through any of the available ring position and further substitution selected from any of the following atom or group such as F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl, 'Hetero-Ar' is independently selected from any of un/substituted heterocycles such as pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl, indolyl, benzotriazolyl, benzoimidazolyl etc and attached through any of the available ring position and further substituted heterocycles contains any of the following atom or group such as F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl, $R_4$, $R_5$, $R_6$, $R_7$, $R_8$, $R_9$, $R_{10}$, $R_{11}$, $R_{12}$, $R_{13}$, $R_{14}$, $R_{15}$, $R_{14}$ and $R_{17}$' are independently selected from any of following substitution such as H, linear alkyl chain $C_1$-$C_{10}$, branched alkyl chain $C_3$-$C_{10}$, un/substituted phenyl ring.

The compound of general formula 1 is useful as anticancer agent.

The compounds of formula 1A and 1B of general formula 1 inhibit PI3K α isoform.

The compounds of formula 1A and 1B of general formula 1 exhibit an in vitro cancer cell line activity.

The compound of formula 1A of general formula 1, wherein said compounds prepared by reacting di-substituted triazine compounds of formula (5) with substituted aryloxy piperidines (6) in an organic solvent N,N-dimethylformamide, in the presence of base potassium carbonate at a room temperature for 24 hrs to obtain the compounds of 1A (1-20) of general formula 1.

The compound of formula 1B of general formula 1, wherein said compounds prepared by reacting di-substituted triazine compounds of formula (8) with substituted aryloxy piperidines (6) in an organic solvent N,N-dimethylformamide in the presence of potassium carbonate at a room temperature for 24 hrs to obtain the compounds of 1B (1-20) of general formula 1.

These compounds, as well as mixtures thereof, isomers, physiologically functionally salt derivatives and drugs thereof, are useful in prevention of or therapy for treating cancer.

Suitable acids for the preparation of the pharmaceutically acceptable salts, but are not limited to hydrochloric acid, sulphuric acid, phosphoric acid, acetic acid, citric acid, oxalic acid, malonic acid, salyilic acid, malic acid, fumaric acid, succinic acid, ascorbic acid, maleic acid and methane-sulfonic acid, boric acid, galactaric acid, gentisic acid, glucoheptonoic acid, D-gluconic acid, D-glucuronic acid, glycolic acid, hyppuric acid.

Suitable bases for the preparation of the pharmaceutically acceptable salts, but are not limited to sodium hydroxide, potassium hydroxide or ammonium hydroxide, ammonia, triethylamine, benethamine, benzathine, choline, deanol, isopropyl amine, L-lysine, L-arginine, morpholine, piperizine, pyrrolidine, pyridine quinoline, isoquinoline, triethanolamine.

The combination of the standard drugs, which are being prescribed presently for anticancer therapy along with the analogs of novel 1,3,5 substituted triazine scaffold with general formula 1, in various proportions and dosage, with the suitable pharmaceutical composition and formulation. The combination of the molecules that are reported as anticancer agents that may be derived from the natural sources viz. marine or terrestrial and the synthetic molecules along with the analogs of novel 1,3,5 substituted triazine scaffold with general formula 1, in various proportions and dosage, with the suitable pharmaceutical composition and formulation.

The compound of formula 1B of general formula 1, wherein said compounds prepared by reacting di substituted triazine compounds of formula (10) with substituted aryl amines (11) in an organic solvent DCM in the presence of acid acetic acid, and reducing agent like a sodium triacetoxy borohydride at a room temperature for 24 hrs to obtain the compounds of 1B (20-40) of general formula 1.

The compound of formula 1B of general formula 1, wherein said compounds prepared by reacting tri-substituted triazine compounds of formula (1B21) with substituted aryl boronic acids compounds of formula (12) in an organic solvent DCM in the presence of triethyl amine and copper acetate at a room temperature for 24 hrs to obtain the compounds of 1B (41-45) of general formula 1.

The compound of formula 1B of general formula 1, wherein said compounds prepared by reacting tri-substituted triazine compounds of formula (15) with substituted aryl amines of formula (11) in an organic solvent DCM in the presence of of acetic acid, and reducing agent sodium triacetoxy borohydride at a room temperature for 24 hrs to obtain the compounds of 1B (45-50) of general formula 1.

The most highly preferred of the compounds of formula 1A and 1B, comprising of:

4-(4-(4-fluorophenoxy)piperidin-1-yl)-N-methyl-6-morpholino-N-phenyl-1,3,5-triazin-2-amine (compound 1A1, Table 1)

4-(4-(2-fluorophenoxy)piperidin-1-yl)-N-methyl-6-morpholino-N-phenyl-1,3,5-triazin-2-amine (compound 1A2, Table 1)

4-(4-(4-fluorophenoxy)piperidin-1-yl)-N-(4-fluorophenyl)-N-methyl-6-morpholino-1,3,5-triazin-2-amine (compound 1A3, Table 1)

2,2,2-trifluoro-N-(4-morpholino-6-(4-phenoxypiperidin-1-yl)-1,3,5-triazin-2-yl)-N-phenylacetamide (compound 1A4, Table 1)

2,2,2-trifluoro-N-(4-fluorophenyl)-N-(4-morpholino-6-(4-phenoxypiperidin-1-yl)-1,3,5-triazin-2-yl)acetamide (compound 1A5, Table 1)

2,2,2-trifluoro-N-(4-(4-(4-fluorophenoxy)piperidin-1-yl)-6-morpholino-1,3,5-triazin-2-yl)-N-(4-fluorophenyl)acetamide (compound 1A6, Table 1)

2,2,2-trifluoro-N-(4-morpholino-6-(4-(4-(trifluoromethyl)phenoxy)piperidin-1-yl)-1,3,5-triazin-2-yl)-N-phenylacetamide (compound 1A7, Table 1)

2,2,2-trifluoro-N-(4-morpholino-6-(4-(p-tolyloxy)piperidin-1-yl)-1,3,5-triazin-2-yl)-N-phenylacetamide (compound 1A8, Table 1)

2,2,2-trifluoro-N-(4-morpholino-6-(4-(4-(trifluoromethoxy)phenoxy)piperidin-1-yl)-1,3,5-triazin-2-yl)-N-phenylacetamide (compound 1A9, Table 1)

2,2,2-trifluoro-N-(4-morpholino-6-(4-(2-(trifluoromethyl)phenoxy)piperidin-1-yl)-1,3,5-triazin-2-yl)-N-phenylacetamide (compound 1A10, Table 1)

2,2,2-trifluoro-N-methyl-N-(4-morpholino-6-(4-phenoxypiperidin-1-yl)-1,3,5-triazin-2-yl)acetamide (compound 1A11, Table 2)

2,2,2-trifluoro-N-(4-morpholino-6-(4-phenoxypiperidin-1-yl)-1,3,5-triazin-2-yl)-N-(2,2,2-trifluoroacetyl)acetamide (compound 1A12, Table 2)

2,2,2-trifluoro-N-(4-(4-(4-fluorophenoxy)piperidin-1-yl)-6-morpholino-1,3,5-triazin-2-yl)-N-(2,2,2-trifluoroacetyl)acetamide (compound 1A13, Table 2)

2,2,2-trifluoro-N-(4-(4-(2-fluorophenoxy)piperidin-1-yl)-6-morpholino-1,3,5-triazin-2-yl)-N-(2,2,2-trifluoroacetyl)acetamide (compound 1A14, Table 2)

2,2,2-trifluoro-N-(4-(4-(4-fluorophenoxy)piperidin-1-yl)-6-morpholino-1,3,5-triazin-2-yl)-N-methylacetamide (compound 1A15, Table 2)

N,N-dimethyl-4-morpholino-6-(4-(p-tolyloxy)piperidin-1-yl)-1,3,5-triazin-2-amine (compound 1A16, Table 2)

4-(4-(4-fluorophenoxy)piperidin-1-yl)-N,N-dimethyl-6-morpholino-1,3,5-triazin-2-amine (compound 1A12, Table 2) (compound 1A17, Table 2)

4-morpholino-6-(4-phenoxypiperidin-1-yl)-N,N-diphenyl-1,3,5-triazin-2-amine (compound 1A18, Table 2)

4-morpholino-N,N-diphenyl-6-(4-(2-(trifluoromethyl)phenoxy)piperidin-1-yl)-1,3,5-triazin-2-amine (compound 1A19, Table 2)

4-morpholino-N,N-diphenyl-6-(4-(4-(trifluoromethoxy)phenoxy)piperidin-1-yl)-1,3,5-triazin-2-amine (compound 1A20, Table 2

4-(4-(2-(difluoromethyl)-1H-benzo[d]imidazol-1-yl)-6-(4-(4-fluorophenoxy)piperidin-1-yl)-1,3,5-triazin-2-yl)morpholine (compound 1B1, Table 3)

4-(4-(2-(difluoromethyl)-1H-benzo[d]imidazol-1-yl)-6-(4-(4-methoxyphenoxy)piperidin-1-yl)-1,3,5-triazin-2-yl)morpholine (compound 1B2, Table 3)

4-(4-(2-(difluoromethyl)-1H-benzo[d]imidazol-1-yl)-6-(4-(4-(trifluoromethoxy)phenoxy)piperidin-1-yl)-1,3,5-triazin-2-yl)morpholine (compound 1B3, Table 3)

4-(4-(2-(difluoromethyl)-1H-benzo[d]imidazol-1-yl)-6-(4-(2-(trifluoromethyl)phenoxy)piperidin-1-yl)-1,3,5-triazin-2-yl)morpholine (compound 1B4, Table 3)

4-(4-(4-(4-chlorophenoxy)piperidin-1-yl)-6-(2-(difluoromethyl)-1H-benzo[d]imidazol-1-yl)-1,3,5-triazin-2-yl)morpholine (compound 1B5, Table 3)

4-(4-(4-(3-chlorophenoxy)piperidin-1-yl)-6-(2-(difluoromethyl)-1H-benzo[d]imidazol-1-yl)-1,3,5-triazin-2-yl)morpholine (compound 1B6, Table 3)

4-(4-(4-(2-chlorophenoxy)piperidin-1-yl)-6-(2-(difluoromethyl)-1H-benzo[d]imidazol-1-yl)-1,3,5-triazin-2-yl)morpholine (compound 1B7, Table 3)

4-(4-(2-(difluoromethyl)-1H-benzo[d]imidazol-1-yl)-6-(4-(3-fluorophenoxy)piperidin-1-yl)-1,3,5-triazin-2-yl)morpholine (compound 1B8, Table 3)

4-(4-(2-(difluoromethyl)-1H-benzo[d]imidazol-1-yl)-6-(4-(2-fluorophenoxy)piperidin-1-yl)-1,3,5-triazin-2-yl)morpholine (compound 1B9, Table 3)

4-(4-(2-(difluoromethyl)-1H-benzo[d]imidazol-1-yl)-6-(4-(p-tolyloxy)piperidin-1-yl)-1,3,5-triazin-2-yl)morpholine (compound 1B10, Table 3)

4-(4-(2-(difluoromethyl)-1H-benzo[d]imidazol-1-yl)-6-(4-(m-tolyloxy)piperidin-1-yl)-1,3,5-triazin-2-yl)morpholine (compound 1B11, Table 4)

4-(4-(2-(difluoromethyl)-1H-benzo[d]imidazol-1-yl)-6-(4-(o-tolyloxy)piperidin-1-yl)-1,3,5-triazin-2-yl)morpholine (compound 1B12, Table 4)

4-(4-(5-fluoro-1H-benzo[d]imidazol-1-yl)-6-(4-(p-tolyloxy)piperidin-1-yl)-1,3,5-triazin-2-yl)morpholine (compound 1B13, Table 4)

4-(4-(5-fluoro-1H-benzo[d]imidazol-1-yl)-6-(4-(4-(trifluoromethyl)phenoxy)piperidin-1-yl)-1,3,5-triazin-2-yl)morpholine (compound 1B14, Table 4)

4-(4-(1H-benzo[d]imidazol-1-yl)-6-(4-(4-(trifluoromethyl)phenoxy)piperidin-1-yl)-1,3,5-triazin-2-yl)morpholine (compound 1B15, Table 4)

4-(4-(1H-benzo[d]imidazol-1-yl)-6-(4-(4-(trifluoromethoxy)phenoxy)piperidin-1-yl)-1,3,5-triazin-2-yl)morpholine (compound 1B16, Table 4)

4-(4-(1H-benzo[d]imidazol-1-yl)-6-(4-(4-fluorophenoxy)piperidin-1-yl)-1,3,5-triazin-2-yl)morpholine (compound 1B17, Table 4)

4-(4-(1H-benzo[d]imidazol-1-yl)-6-(4-(2-fluorophenoxy)piperidin-1-yl)-1,3,5-triazin-2-yl)morpholine (compound 1B18, Table 4)

4-(4-(1H-benzo[d]imidazol-1-yl)-6-(4-(2-chlorophenoxy)piperidin-1-yl)-1,3,5-triazin-2-yl)morpholine (compound 1B19, Table 4)

4-(4-(1H-benzo[d]imidazol-1-yl)-6-(4-(2-(trifluoromethyl)phenoxy)piperidin-1-yl)-1,3,5-triazin-2-yl)morpholine (compound 1B20, Table 4)

1-(4-(2-(difluoromethyl)-1H-benzo[d]imidazol-1-yl)-6-morpholino-1,3,5-triazin-2-yl)-N-(4-fluorophenyl)piperidin-4-amine (compound 1B21, Table 5)

1-(4-(2-(difluoromethyl)-1H-benzo[d]imidazol-1-yl)-6-morpholino-1,3,5-triazin-2-yl)-N-(4-(trifluoromethyl)phenyl)piperidin-4-amine (compound 1B22, Table 5)

1-(4-(2-(difluoromethyl)-1H-benzo[d]imidazol-1-yl)-6-morpholino-1,3,5-triazin-2-yl)-N-(4-(trifluoromethoxy)phenyl)piperidin-4-amine (compound 1B23, Table 5)

1-(4-(2-(difluoromethyl)-1H-benzo[d]imidazol-1-yl)-6-morpholino-1,3,5-triazin-2-yl)-N-(4-methoxyphenyl)piperidin-4-amine (compound 1B24, Table 5)

N-(4-bromophenyl)-1-(4-(2-(difluoromethyl)-1H-benzo[d]imidazol-1-yl)-6-morpholino-1,3,5-triazin-2-yl)piperidin-4-amine (compound 1B25, Table 5)

N-(3,4-dichlorophenyl)-1-(4-(2-(difluoromethyl)-1H-benzo[d]imidazol-1-yl)-6-morpholino-1,3,5-triazin-2-yl)piperidin-4-amine (compound 1B26, Table 5)

1-(4-(2-(difluoromethyl)-1H-benzo[d]imidazol-1-yl)-6-morpholino-1,3,5-triazin-2-yl)-N-(2-fluorophenyl)piperidin-4-amine (compound 1B27, Table 5)

1-(4-(2-(difluoromethyl)-1H-benzo[d]imidazol-1-yl)-6-morpholino-1,3,5-triazin-2-yl)-N-(2-methoxyphenyl)piperidin-4-amine (compound 1B28, Table 5)

1-(4-(2-(difluoromethyl)-1H-benzo[d]imidazol-1-yl)-6-morpholino-1,3,5-triazin-2-yl)-N-(2-(trifluoromethyl)phenyl)piperidin-4-amine (compound 1B29, Table 5)

1-(4-(2-(difluoromethyl)-1H-benzo[d]imidazol-1-yl)-6-morpholino-1,3,5-triazin-2-yl)-N-(p-tolyl)piperidin-4-amine (compound 1B30, Table 5)

1-(4-(2-(difluoromethyl)-1H-benzo[d]imidazol-1-yl)-6-morpholino-1,3,5-triazin-2-yl)-N-(3-methoxyphenyl)piperidin-4-amine (compound 1B31, Table 5)

1-(4-(2-(difluoromethyl)-1H-benzo[d]imidazol-1-yl)-6-morpholino-1,3,5-triazin-2-yl)-N-(o-tolyl)piperidin-4-amine (compound 1B32, Table 6)

1-(4-(2-(difluoromethyl)-5-fluoro-1H-benzo[d]imidazol-1-yl)-6-morpholino-1,3,5-triazin-2-yl)-N-(p-tolyl)piperidin-4-amine (compound 1B33, Table 6)

1-(4-(2-(difluoromethyl)-5-fluoro-1H-benzo[d]imidazol-1-yl)-6-morpholino-1,3,5-triazin-2-yl)-N-(4-(trifluoromethyl)phenyl)piperidin-4-amine (compound 1B34, Table 6)

1-(4-(2-(difluoromethyl)-1H-benzo[d]imidazol-1-yl)-6-morpholino-1,3,5-triazin-2-yl)-N-(4-(trifluoromethyl)phenyl)piperidin-4-amine (compound 1B35, Table 6)

1-(4-(2-(difluoromethyl)-1H-benzo[d]imidazol-1-yl)-6-morpholino-1,3,5-triazin-2-yl)-N-(4-(trifluoromethoxy)phenyl)piperidin-4-amine (compound 1B36, Table 6)

1-(4-(2-(difluoromethyl)-1H-benzo[d]imidazol-1-yl)-6-morpholino-1,3,5-triazin-2-yl)-N-(4-fluorophenyl)piperidin-4-amine (compound 1B37, Table 6)

1-(4-(2-(difluoromethyl)-1H-benzo[d]imidazol-1-yl)-6-morpholino-1,3,5-triazin-2-yl)-N-(2-fluorophenyl)piperidin-4-amine (compound 1B38, Table 6)

N-(2-chlorophenyl)-1-(4-(2-(difluoromethyl)-1H-benzo[d]imidazol-1-yl)-6-morpholino-1,3,5-triazin-2-yl)piperidin-4-amine (compound 1B39, Table 6)

1-(4-(2-(difluoromethyl)-1H-benzo[d]imidazol-1-yl)-6-morpholino-1,3,5-triazin-2-yl)-N-(2-(trifluoromethyl)phenyl)piperidin-4-amine (compound 1B40, Table 6)

1-(4-(2-(difluoromethyl)-1H-benzo[d]imidazol-1-yl)-6-morpholino-1,3,5-triazin-2-yl)-N,N-bis(4-fluorophenyl)piperidin-4-amine (compound 1B41, Table 7)

N-(4-bromophenyl)-1-(4-(2-(difluoromethyl)-1H-benzo[d]imidazol-1-yl)-6-morpholino-1,3,5-triazin-2-yl)-N-(4-fluorophenyl)piperidin-4-amine (compound 1B42, Table 7)

1-(4-(2-(difluoromethyl)-1H-benzo[d]imidazol-1-yl)-6-morpholino-1,3,5-triazin-2-yl)-N-(4-fluorophenyl)-N-(4-(trifluoromethyl)phenyl)piperidin-4-amine (compound 1B43, Table 7)

N-(4-chlorophenyl)-1-(4-(2-(difluoromethyl)-1H-benzo[d]imidazol-1-yl)-6-morpholino-1,3,5-triazin-2-yl)-N-(4-fluorophenyl)piperidin-4-amine (compound 1B44, Table 7)

N-(1-(4-(2-(difluoromethyl)-1H-benzo[d]imidazol-1-yl)-6-morpholino-1,3,5-triazin-2-yl)piperidin-4-yl)-N-(4-fluorophenyl)-3-(trifluoromethyl)pyridin-4-amine (compound 1B45, Table 7)

1-(4-(2-(difluoromethyl)-1H-indol-1-yl)-6-morpholino-1,3,5-triazin-2-yl)-N-(4-fluorophenyl)piperidin-4-amine (compound 1B46, Table 7)

1-(4-(2-(difluoromethyl)-1H-indol-1-yl)-6-morpholino-1,3,5-triazin-2-yl)-N-(4-methoxyphenyl)piperidin-4-amine (compound 1B47, Table 7)

1-(4-(2-(difluoromethyl)-1H-indol-1-yl)-6-morpholino-1,3,5-triazin-2-yl)-N-(4-(trifluoromethoxy)phenyl)piperidin-4-amine (compound 1B48, Table 7)

1-(4-(2-(difluoromethyl)-1H-indol-1-yl)-6-morpholino-1,3,5-triazin-2-yl)-N-(4-(trifluoromethyl)phenyl)piperidin-4-amine (compound 1B49, Table 7)

N-(4-chlorophenyl)-1-(4-(2-(difluoromethyl)-1H-indol-1-yl)-6-morpholino-1,3,5-triazin-2-yl)piperidin-4-amine (compound 1B50, Table 7)

The invention is further described by reference to following examples which are intended to illustrate, not to limit the scope of the invention.

Example 1

General Procedure for the Preparation of Compounds (IA1-20):

Cynuric chloride (1) (10 g, 54.2 mmol, 1.0 eq) was substituted by morpholine (7) (4.72 ml, 5.42 mmol, 1.0 eq) in methylene chloride (60 ml), at −50° C. for 20 min to obtain intermediate (3). The intermediate (3) (5 g, 1.0 eq) on further treatment with di-substituted amine (4) (1.4 eq) in presence of $K_2CO_3$ (1.44 eq) in DMF (20 ml), at −5° C. for 30 min and then at room temperature for 4 h led to intermediate (5). To the solution of intermediate (5) (100 mg, 1.0 eq) in DMF (3 ml) were added $K_2CO_3$ (1.4 eq) and substituted aryloxy piperidines (6) (1.44 eq). This resulting reaction mixture was stirred at room temperature for 24 h. The thus-obtained mixture was poured into water (30 ml) and extracted with ethyl acetate twice washed with 2N HCl solution and dried under vacuo. This crude product was purified by silica gel column chromatography using a ethyl acetate and hexane mixture as solvent to obtained the compound of formula 1A(1-20).

Example 2

General Procedure for the Preparation of Compounds (IB1-20):

Cynuric chloride (1) (10 g, 54.2 mmol, 1.0 eq) was substituted by morpholine (7) (4.72 ml, 5.42 mmol, 1.0 eq) in methylene chloride (60 ml), at −50° C. for 20 min to obtain intermediate (3). The intermediate (3) (5 g, 1.0 eq) on further treatment with di-substituted benzimidazole (7) (1.4 eq) in presence of $K_2CO_3$ (1.44 eq) in DMF (20 ml), at −5° C. for 30 min and then at room temperature for 4 h led to intermediate (8). To the solution of intermediate (8) (100 mg, 1.0 eq) in DMF (3 ml) are added $K_2CO_3$ (1.4 eq) and substituted aryloxy piperidines (6) (1.44 eq). This resulting reaction mixture was stirred at room temperature for 24 h. The thus-obtained mixture was poured into water (30 ml) and extracted with ethyl acetate twice washed with 2N HCl solution and dried under vacuo. This crude product was purified by silica gel column chromatography using an ethyl acetate and hexane mixture as solvent to obtained the compounds formula (1B1-20).

Example 3

General Procedure for the Preparation of Compounds (IB21-40):

The intermediate (8) (5 g, 1.0 eq) on reaction with piperidone (9) (1.4 eq) in presence of $K_2CO_3$ (1.44 eq) in DMF (20 ml), at room temperature for 24 h led to the formation of intermediate (10). To the solution of intermediate (10) (100 mg, 1.0 eq) in dichloromethane (3 ml) are added acetic acid (1 eq) and substituted primary aromatic amines (11) (1 eq). This resulting reaction mixture was stirred at room temperature for 6 h and then added Sodium triacetoxy borohydride (Na(OAC)$_3$BH) (1 eq). This resulting reaction mixture again stirred at room temperature for 24 h. The thus-obtain mixture was poured into water (30 ml) and extracted with ethyl acetate and dried under vacuo. This crude product was purified by silica gel column chromatography using an ethyl acetate and hexane mixture as solvent to obtain the compounds of formula (1B21-40).

Example 4

General Procedure for the Preparation of Compounds (IB41-45):

Take the (IB21) (100 mg, 1.0 eq) on reaction with substituted aryl boronic acid (12) (2 eq) and copper acetate (20 mole %) in dichloromethane solvent at room temperature. To this reaction mixture added the triethylamine (1 eq). This resulting mixture stirred at room temperature for 24 h. The thus-obtained mixture was poured into water (30 ml) and extracted with ethyl acetate and dried under vacuo. This crude product was purified by silica gel column chromatography using an ethyl acetate and hexane mixture as solvent to obtained the compounds formula (1B41-45).

Example 5

General Procedure for the Preparation of Compounds (IB46-50):

Cynuric chloride (1) (10 g, 54.2 mmol, 1.0 eq) was substituted by morpholine (7) (4.72 ml, 5.42 mmol, 1.0 eq) in methylene chloride (60 ml), at −50° C. for 20 min to obtain intermediate (3). The intermediate (3) (5 g, 1.0 eq) on further treatment with substituted indole (13) (1.4 eq) in presence of K$_2$CO$_3$ (1.44 eq) in DMF (20 ml), at −5° C. for 30 min and further stirring at room temperature for 4 h led to intermediate (14). The intermediate (14) (5 g, 1.0 eq) on reaction with piperidone (9) (1.4 eq) in presence of K$_2$CO$_3$ (1.44 eq) in DMF (20 ml), at room temperature for 24 h led to intermediate (15). To the solution of intermediate (15) (100 mg, 1.0 eq) in Dichloromethane (3 ml) are added acetic acid (1 eq) and substituted primary aromatic amines (11) (1 eq). This resulting reaction mixture was stirred at room temperature for 6 h and then added Sodium triacetoxy borohydride (Na(OAC)$_3$BH) (1 eq). This resulting mixture was stirred again at room temperature for 24 h. The thus-obtained mixture was poured into water (30 ml) and extracted with ethyl acetate and dried under vacuo. This crude product was purified by silica gel column chromatography using an ethyl acetate and hexane mixture as solvent to obtain the compounds of formula (1B46-50).

4-(4-(4-fluorophenoxy)piperidin-1-yl)-N-methyl-6-morpholino-N-phenyl-1,3,5-triazin-2-amine (compound 1A1, Table 1, FIG. 1)

$^1$H NMR (400 MHz, CDCl$_3$) δ 7.26 (t, J=7.5 Hz, 2H), 7.08-6.91 (m, 7H), 4.53-4.43 (m, 1H), 3.77 (t, J=4.9 Hz, 4H), 3.52-3.42 (m, 4H), 3.40 (t, J=4.8 Hz, 2H), 3.32 (dt, J=12.3, 5.3 Hz, 2H), 2.15 (dqd, J=12.7, 5.4, 2.3 Hz, 2H), 1.88 (dqd, J=12.8, 5.4, 2.2 Hz, 2H) Mass: ESI [M+1]: 465.

4-(4-(2-fluorophenoxy)piperidin-1-yl)-N-methyl-6-morpholino-N-phenyl-1,3,5-triazin-2-amine (compound 1A2, Table 1, FIG. 1)

$^1$H NMR (400 MHz, CDCl$_3$) δ 7.26 (t, J=7.5 Hz, 2H), 7.09-6.84 (m, 7H), 4.31 (p, J=7.2 Hz, 1H), 3.53 (t, J=4.9 Hz, 2H), 3.39 (ddq, J=64.5, 12.3, 6.1 Hz, 6H), 2.34-2.20 (m, 2H), 1.92 (qd, J=12.4, 6.1 Hz, 2H) Mass: ESI [M+1]: 465.

4-(4-(4-fluorophenoxy)piperidin-1-yl)-N-(4-fluorophenyl)-N-methyl-6-morpholino-1,3,5-triazin-2-amine (compound 1A3, Table 1, FIG. 1)

$^1$H NMR (400 MHz, CDCl$_3$) δ 7.09-6.87 (m, 8H), 4.54-4.40 (m, 1H), 3.77 (t, J=4.8 Hz, 4H), 3.52-3.24 (m, 8H), 3.01 (s, 3H), 2.20-2.07 (m, 2H), 1.99-1.80 (m, 2H) Mass: ESI [M+1]: 483.

2,2,2-trifluoro-N-(4-morpholino-6-(4-phenoxypiperidin-1-yl)-1,3,5-triazin-2-yl)-N-phenylacetamide (compound 1A4, Table 1, FIG. 1)

$^1$H NMR (400 MHz, CDCl$_3$) δ 7.41-7.14 (m, 6H), 7.14-6.80 (m, 4H), 4.39 (tt, J=7.9, 3.8 Hz, 1H), 3.79 (t, J=4.8 Hz, 4H), 3.54 (t, J=4.9 Hz, 2H), 3.47-3.20 (m, 6H), 2.30-2.12 (m, 2H), 1.90 (dqd, J=11.1, 5.4, 1.9 Hz, 2H) Mass: ESI [M+1]: 529.

2,2,2-trifluoro-N-(4-fluorophenyl)-N-(4-morpholino-6-(4-phenoxypiperidin-1-yl)-1,3,5-triazin-2-yl)acetamide (compound 1A5, Table 1, FIG. 1)

$^1$H NMR (400 MHz, CDCl$_3$) δ 7.34-7.14 (m, 4H), 7.09 (t, J=7.8 Hz, 2H), 6.99-6.82 (m, 3H), 4.38 (tt, J=8.0, 4.0 Hz, 1H), 3.59-3.37 (m, 6H), 3.29 (dt, J=12.3, 5.3 Hz, 2H), 2.27-2.10 (m, 2H), 1.91 (tdd, J=11.4, 5.4, 1.8 Hz, 2H) Mass: ESI [M+1]: 547.

2,2,2-trifluoro-N-(4-(4-(4-fluorophenoxy)piperidin-1-yl)-6-morpholino-1,3,5-triazin-2-yl)-N-(4-fluorophenyl)acetamide (compound 1A6, Table 1, FIG. 1)

$^1$H NMR (400 MHz, CDCl$_3$) δ 7.31-7.19 (m, 2H), 7.04 (dt, J=49.3, 7.8 Hz, 4H), 6.94-6.79 (m, 2H), 4.09 (p, J=7.4 Hz, 1H), 3.78 (t, J=4.9 Hz, 4H), 3.57-3.37 (m, 6H), 3.21 (dt, J=12.2, 5.5 Hz, 2H), 2.14 (ddt, J=12.9, 7.5, 5.5 Hz, 2H), 1.92 (ddt, J=12.8, 7.5, 5.5 Hz, 2H) Mass: ESI [M+1]: 565.

2,2,2-trifluoro-N-(4-morpholino-6-(4-(4-(trifluoromethyl)phenoxy)piperidin-1-yl)-1,3,5-triazin-2-yl)-N-phenylacetamide (compound 1A7, Table 1, FIG. 1)

$^1$H NMR (400 MHz, CDCl$_3$) δ 7.50 (d, J=7.5 Hz, 2H), 7.42-7.21 (m, 4H), 7.14-7.04 (m, 1H), 6.87 (d, J=7.5 Hz, 2H), 4.40 (tt, J=8.0, 4.0 Hz, 1H), 3.79 (t, J=4.8 Hz, 4H), 3.54 (t, J=4.8 Hz, 2H), 3.45-3.18 (m, 6H), 2.32-2.10 (m, 2H), 1.99-1.80 (m, 2H) Mass: ESI [M+1]: 597.

2,2,2-trifluoro-N-(4-morpholino-6-(4-(p-tolyloxy)piperidin-1-yl)-1,3,5-triazin-2-yl)-N-phenylacetamide (compound 1A8, Table 1, FIG. 1)

$^1$H NMR (400 MHz, CDCl$_3$) δ 7.42-7.21 (m, 4H), 7.17-7.02 (m, 3H), 6.84 (d, J=7.5 Hz, 2H), 4.08 (p, J=7.4 Hz, 1H), 3.78 (t, J=4.9 Hz, 4H), 3.59-3.39 (m, 6H), 3.19 (dt, J=12.4,

2,2,2-trifluoro-N-(4-morpholino-6-(4-(4-(trifluoromethoxy)phenoxy)piperidin-1-yl)-1,3,5-triazin-2-yl)-N-phenylacetamide (compound 1A9, Table 1, FIG. 1)

$^1$H NMR (400 MHz, CDCl$_3$) δ 7.39-7.21 (m, 4H), 7.14-7.06 (m, 1H), 6.95 (dd, J=39.7, 7.5 Hz, 4H), 4.38 (tt, J=8.0, 4.1 Hz, 1H), 3.78 (t, J=4.9 Hz, 4H), 3.57-3.36 (m, 6H), 3.29 (dt, J=12.3, 5.4 Hz, 2H), 2.30-2.10 (m, 2H), 1.99-1.80 (m, 2H) Mass: ESI [M+1]: 613.

2,2,2-trifluoro-N-(4-morpholino-6-(4-(2-(trifluoromethyl)phenoxy)piperidin-1-yl)-1,3,5-triazin-2-yl)-N-phenylacetamide (compound 1A10, Table 1, FIG. 1)

$^1$H NMR (400 MHz, CDCl$_3$) δ 7.56 (dd, J=7.4, 1.5 Hz, 1H), 7.31 (ddd, J=33.5, 7.5, 1.4 Hz, 5H), 7.17-6.89 (m, 3H), 4.68 (p, J=3.1 Hz, 1H), 3.78 (t, J=4.9 Hz, 4H), 3.59-3.32 (m, 6H), 3.18 (dt, J=12.4, 5.6 Hz, 2H), 2.22 (dtd, J=12.2, 5.6, 2.9 Hz, 2H), 2.00 (dtd, J=12.4, 5.6, 2.9 Hz, 2H) Mass: ESI [M+1]: 597.

2,2,2-trifluoro-N-methyl-N-(4-morpholino-6-(4-phenoxypiperidin-1-yl)-1,3,5-triazin-2-yl)acetamide (compound 1A11, Table 2, FIG. 1)

$^1$H NMR (400 MHz, CDCl$_3$) δ 7.26 (t, J=7.5 Hz, 2H), 7.06-6.86 (m, 3H), 4.14 (p, J=7.5 Hz, 1H), 3.78 (t, J=4.9 Hz, 4H), 3.57-3.39 (m, 6H), 3.32 (s, 3H), 3.20 (dt, J=12.4, 5.7 Hz, 2H), 2.22-2.05 (m, 2H), 2.00-1.87 (m, 2H) Mass: ESI [M+1]: 467.

2,2,2-trifluoro-N-(4-morpholino-6-(4-phenoxypiperidin-1-yl)-1,3,5-triazin-2-yl)-N-(2,2,2-trifluoroacetyl)acetamide (compound 1A12, Table 2, FIG. 1)

$^1$H NMR (400 MHz, CDCl$_3$) δ 7.23 (t, J=7.5 Hz, 2H), 6.99-6.79 (m, 3H), 4.38 (tt, J=7.6, 3.7 Hz, 1H), 3.78 (t, J=4.9 Hz, 4H), 3.55-3.34 (m, 6H), 3.29 (dt, J=12.4, 5.3 Hz, 2H), 2.28-2.05 (m, 2H), 2.00-1.77 (m, 2H) Mass: ESI [M+1]: 549.

2,2,2-trifluoro-N-(4-(4-(4-fluorophenoxy)piperidin-1-yl)-6-morpholino-1,3,5-triazin-2-yl)-N-(2,2,2-trifluoroacetyl)acetamide (compound 1A13, Table 2, FIG. 1)

$^1$H NMR (400 MHz, CDCl$_3$) δ 7.11-6.84 (m, 4H), 4.12 (p, J=7.6 Hz, 1H), 3.78 (t, J=4.8 Hz, 4H), 3.54-3.34 (m, 6H), 3.21 (dt, J=12.3, 5.6 Hz, 2H), 2.14 (ddt, J=13.0, 7.6, 5.5 Hz, 2H), 1.95 (ddt, J=13.0, 7.6, 5.6 Hz, 2H) Mass: ESI [M+1]: 567.

2,2,2-trifluoro-N-(4-(4-(2-fluorophenoxy)piperidin-1-yl)-6-morpholino-1,3,5-triazin-2-yl)-N-(2,2,2-trifluoroacetyl)acetamide (compound 1A14, Table 2, FIG. 1)

$^1$H NMR (400 MHz, CDCl$_3$) δ 7.14-6.82 (m, 4H), 4.26 (p, J=7.6 Hz, 1H), 3.78 (t, J=4.9 Hz, 4H), 3.60-3.34 (m, 6H), 3.18 (dt, J=12.4, 5.5 Hz, 2H), 2.17 (ddt, J=12.9, 7.5, 5.5 Hz, 2H), 2.00 (ddt, J=12.8, 7.5, 5.5 Hz, 2H) Mass: ESI [M+1]: 567.

2,2,2-trifluoro-N-(4-(4-(4-fluorophenoxy)piperidin-1-yl)-6-morpholino-1,3,5-triazin-2-yl)-N-methylacetamide (compound 1A15, Table 1, FIG. 1)

$^1$H NMR (400 MHz, CDCl$_3$) δ 7.01 (t, J=7.7 Hz, 2H), 6.96-6.88 (m, 2H), 4.61-4.52 (m, 1H), 3.78 (t, J=4.8 Hz, 4H), 3.56-3.41 (m, 6H), 3.39-3.31 (m, 5H), 2.22 (dqd, J=12.9, 5.4, 2.3 Hz, 2H), 1.94 (dqd, J=12.9, 5.4, 2.3 Hz, 2H) Mass: ESI [M+1]: 485.

N,N-dimethyl-4-morpholino-6-(4-(p-tolyloxy)piperidin-1-yl)-1,3,5-triazin-2-amine (compound 1A16, Table 1, FIG. 1)

$^1$H NMR (400 MHz, CDCl$_3$) δ 7.12 (d, J=7.5 Hz, 2H), 6.85 (d, J=7.5 Hz, 2H), 4.43-4.34 (m, 1H), 3.78 (t, J=4.8 Hz, 4H), 3.52 (t, J=4.9 Hz, 2H), 3.48-3.39 (m, 4H), 3.30 (dt, J=12.4, 5.3 Hz, 2H), 2.99 (s, 6H), 2.33 (s, 3H), 2.24-2.13 (m, 2H), 1.89 (dqd, J=12.8, 5.4, 2.0 Hz, 2H) Mass: ESI [M+1]. 399.

4-(4-(4-fluorophenoxy)piperidin-1-yl)-N,N-dimethyl-6-morpholino-1,3,5-triazin-2-amine (compound 1A17, Table 2, FIG. 1)

$^1$H NMR (400 MHz, CDCl$_3$) δ 7.12 (d, J=7.5 Hz, 2H), 6.85 (d, J=7.5 Hz, 2H), 4.43-4.34 (m, 1H), 3.78 (t, J=4.8 Hz, 4H), 3.52 (t, J=4.9 Hz, 2H), 3.48-3.39 (m, 4H), 3.30 (dt, J=12.4, 5.3 Hz, 2H), 2.99 (s, 6H), 2.24-2.13 (m, 2H), 1.89 (dqd, J=12.8, 5.4, 2.0 Hz) Mass: ESI [M+1]: 403.

4-morpholino-6-(4-phenoxypiperidin-1-yl)-N,N-diphenyl-1,3,5-triazin-2-amine (compound 1A18, Table 2, FIG. 1)

$^1$H NMR (400 MHz, CDCl$_3$) δ 7.25 (td, J=7.7, 1.1 Hz, 6H), 7.04-6.86 (m, 9H), 4.50-4.41 (m, 1H), 3.44 (ddd, J=14.0, 10.1, 5.0 Hz, 4H), 3.32 (dt, J=12.3, 5.3 Hz, 2H), 3.98-2.00 (m, 14H), 3.51-2.00 (m, 8H), 2.17 (dqd, J=12.9, 5.4, 2.2 Hz, 2H), 1.91 (dqd, J=12.8, 5.4, 2.2 Hz, 2H) Mass: ESI [M+1]: 509.

4-morpholino-N,N-diphenyl-6-(4-(2-(trifluoromethyl)phenoxy)piperidin-1-yl)-1,3,5-triazin-2-amine (compound 1A19, Table 2, FIG. 1)

$^1$H NMR (400 MHz, CDCl$_3$) δ 7.51 (dd, J=7.4, 1.5 Hz, 1H), 7.33-7.21 (m, 5H), 7.05-6.86 (m, 8H), 4.10 (p, J=7.5 Hz, 1H), 3.78 (t, J=4.5 Hz, 4H), 3.58-3.49 (m, 4H), 3.40 (t, J=4.5 Hz, 2H), 3.20 (dt, J=12.3, 5.4 Hz, 2H), 2.19 (ddt, J=12.8, 7.4, 5.5 Hz, 2H), 1.94 (ddt, J=12.8, 7.4, 5.5 Hz, 2H) Mass: ESI [M+1]: 577.

4-morpholino-N,N-diphenyl-6-(4-(4-(trifluoromethoxy)phenoxy)piperidin-1-yl)-1,3,5-triazin-2-amine (compound 1A20, Table 2, FIG. 1)

$^1$H NMR (400 MHz, CDCl$_3$) δ 7.26 (t, J=7.5 Hz, 4H), 7.05-6.94 (m, 6H), 6.89 (q, J=7.5 Hz, 4H), 4.48 (p, J=2.7 Hz, 1H), 3.78 (t, J=4.8 Hz, 4H), 3.56-3.41 (m, 6H), 3.30 (dt, J=12.4, 5.4 Hz, 2H), 2.13 (dtd, J=12.4, 5.4, 2.8 Hz, 2H), 1.87 (dtd, J=12.4, 5.4, 2.8 Hz, 2H) Mass: ESI [M+1]: 593.

4-(4-(2-(difluoromethyl)-1H-benzo[d]imidazol-1-yl)-6-(4-(4-fluorophenoxy)piperidin-1-yl)-1,3,5-triazin-2-yl)morpholine (compound 1B1, Table 3, FIG. 2)

$^1$H NMR (400 MHz, CDCl$_3$) δ 8.35 (dd, J=7.2, 1.2 Hz, 1H), 7.89 (d, J=7.4 Hz, 1H), 7.65 (d, J=53.7 Hz, 1H), 7.49-7.33 (m, 2H), 7.07-6.83 (m, 4H), 4.53 (tt, J=6.2, 3.1 Hz, 1H), 4.06 (d, J=4.8 Hz, 2H), 3.84 (dd, J=33.6, 4.7 Hz, 10H), 1.95 (d, J=40.2 Hz, 4H). Mass: ESI [M+1]: 526.

4-(4-(2-(difluoromethyl)-1H-benzo[d]imidazol-1-yl)-6-(4-(4-methoxyphenoxy)piperidin-1-yl)-1,3,5-triazin-2-yl)morpholine (compound 1B2, Table 3, FIG. 2)

$^1$H NMR (400 MHz, CDCl$_3$): δ8.36 (d, J=8 Hz, 1H), 7.90 (d, J=8 Hz, 1H), 7.73 (t, J=54, 1H), 7.45 (m, 2H), 6.92 (m, 4H), 4.50 (m, 1H), 4.08 (d, J=4 Hz, 2H), 3.89 (dd, J=6 Hz, J=39 Hz, 13H), 1.99 (dd, J=1 Hz, J=31 Hz, 4H). Mass: ESI [M+1]: 538.

4-(4-(2-(difluoromethyl)-1H-benzo[d]imidazol-1-yl)-6-(4-(trifluoromethoxy)phenoxy) piperidin-1-yl)-1,3,5-triazin-2-yl)morpholine (compound 1B3, Table 3, FIG. 2)

$^1$H NMR (400 MHz, CDCl$_3$) δ8.36 (d, J=8 Hz, 1H), 7.90 (d, J=8 Hz, 1H), 7.73 (t, J=54, 1H), 7.45 (m, 2H), 6.92 (m, 4H), 4.50 (m, 1H), 4.08 (d, J=4 Hz, 2H), 3.89 (dd, J=6 Hz, J=39 Hz, 13H), 1.99 (dd, J=1 Hz, J=31 Hz, 4H). Mass: ESI [M+1]:592.

4-(4-(2-(difluoromethyl)-1H-benzo[d]imidazol-1-yl)-6-(4-(2-(trifluoromethyl)phenoxy) piperidin-1-yl)-1,3,5-triazin-2-yl)morpholine (compound 1B4, Table 3, FIG. 2)

$^1$H NMR (400 MHz, CDCl$_3$) δ 8.35 (d, J=7.9 Hz, 1H), 7.89 (d, J=7.1 Hz, 1H), 7.67 (d, J=41.7 Hz, 1H), 7.59 (d, J=3.9 Hz, 1H), 7.54-7.35 (m, 3H), 7.01 (dd, J=15.2, 8.7 Hz, 2H), 4.91-4.71 (m, 1H), 4.22 (d, J=10.4 Hz, 2H), 3.84 (d, J=35.7 Hz, 9H), 2.00 (dd, J=25.1, 14.4 Hz, 4H). Mass: ESI [M+1]:576.

4-(4-(4-chlorophenoxy)piperidin-1-yl)-6-(2-(difluoromethyl)-1H-benzo[d]imidazol-1-yl)-1,3,5-triazin-2-yl)morpholine (compound 1B5, Table 3, FIG. 2)

$^1$H NMR (400 MHz, CDCl$_3$) δ 8.34 (d, J=7.2 Hz, 1H), 7.89 (d, J=7.0 Hz, 1H), 7.65 (d, J=53.6 Hz, 1H), 7.50-7.33 (m, 2H), 7.29-7.23 (m, 2H), 6.88 (dd, J=6.6, 2.3 Hz, 2H), 4.62-4.52 (m, 1H), 4.05 (d, J=2.1 Hz, 2H), 3.84 (d, J=36.6 Hz, 9H), 1.96 (d, J=39.3 Hz, 4H). Mass: ESI [M+1]:542.

4-(4-(4-(3-chlorophenoxy)piperidin-1-yl)-6-(2-(difluoromethyl)-1H-benzo[d]imidazol-1-yl)-1,3,5-triazin-2-yl)morpholine (compound 1B6, Table 3, FIG. 2)

$^1$H NMR (400 MHz, CDCl$_3$) δ 8.35 (d, J=7.6 Hz, 1H), 7.89 (d, J=7.4 Hz, 1H), 7.66 (d, J=53.6 Hz, 1H), 7.46-7.36 (m, 2H), 7.22 (t, J=8.4 Hz, 1H), 6.99-6.94 (m, 2H), 6.84 (d, J=9.2 Hz, 1H), 4.61 (dd, J=6.1, 3.0 Hz, 1H), 4.15-3.97 (m, 2H), 3.89 (ddd, J=37.4, 19.6, 4.2 Hz, 10H), 1.97 (d, J=34.7 Hz, 4H). Mass: ESI [M+1]: 542.

4-(4-(4-(2-chlorophenoxy)piperidin-1-yl)-6-(2-(difluoromethyl)-1H-benzo[d]imidazol-1-yl)-1,3,5-triazin-2-yl)morpholine (compound 1B7, Table 3, FIG. 2)

$^1$H NMR (400 MHz, CDCl$_3$) δ 8.36 (d, J=7.4 Hz, 2H), 7.88 (d, J=6.9 Hz, 2H), 7.66 (d, J=53.6 Hz, 2H), 7.50-7.28 (m, 7H), 7.22 (t, J=12.5 Hz, 2H), 7.06-6.84 (m, 4H), 4.80-4.61 (m, 2H), 4.03 (d, J=24.4 Hz, 8H), 3.83 (d, J=34.1 Hz, 15H), 1.99 (s, 8H). Mass: ESI [M+1]:542.

4-(4-(2-(difluoromethyl)-1H-benzo[d]imidazol-1-yl)-6-(4-(3-fluorophenoxy)piperidin-1-yl)-1,3,5-triazin-2-yl)morpholine (compound 1B8, Table 3, FIG. 2)

$^1$H NMR (400 MHz, CDCl$_3$) δ 8.35 (d, J=7.6 Hz, 1H), 7.89 (d, J=7.4 Hz, 1H), 7.66 (d, J=53.6 Hz, 1H), 7.46-7.36 (m, 2H), 7.22 (t, J=8.4 Hz, 1H), 6.99-6.94 (m, 2H), 6.84 (d, J=9.2 Hz, 1H), 4.61 (dd, J=6.1, 3.0 Hz, 1H), 4.15-3.97 (m, 2H), 3.89 (ddd, J=37.4, 19.6, 4.2 Hz, 10H), 1.97 (d, J=34.7 Hz, 4H). Mass: ESI [M+1]: 526.

4-(4-(2-(difluoromethyl)-1H-benzo[d]imidazol-1-yl)-6-(4-(2-fluorophenoxy)piperidin-1-yl)-1,3,5-triazin-2-yl)morpholine (compound 1B9, Table 3, FIG. 2)

$^1$H NMR (400 MHz, CDCl$_3$): δ8.36 (d, J=8 Hz, 1H), 7.90 (d, J=8 Hz, 1H), 7.73 (t, J=54, 1H), 7.45 (m, 2H), 7.21 (d, J=3 Hz, 1H), 7.01 (d, J=3 Hz, 1H), 6.96 (m, 2H), 4.50 (m, 1H), 4.08 (d, J=4 Hz, 2H), 3.89 (dd, J=6 Hz, J=39 Hz, 10H), 1.99 (dd, J=1 Hz, J=31 Hz, 4H). Mass: ESI [M+1]:526.

4-(4-(2-(difluoromethyl)-1H-benzo[d]imidazol-1-yl)-6-(4-(p-tolyloxy)piperidin-1-yl)-1,3,5-triazin-2-yl)morpholine (compound 1B10, Table 3, FIG. 2)

$^1$H NMR (400 MHz, CDCl$_3$) δ 8.35 (d, J=7.5 Hz, 1H), 7.89 (d, J=7.3 Hz, 1H), 7.66 (d, J=53.6 Hz, 1H), 7.43-7.35 (m, 2H), 7.11 (d, J=8.2 Hz, 2H), 6.86 (d, J=8.4 Hz, 2H), 4.65-4.48 (m, 1H), 4.15-3.98 (m, 2H), 3.87 (t, J=25.4 Hz, 9H), 2.30 (s, 3H), 2.05-1.87 (m, 4H). Mass: ESI [M+1]:522.

4-(4-(2-(difluoromethyl)-1H-benzo[d]imidazol-1-yl)-6-(4-(m-tolyloxy)piperidin-1-yl)-1,3,5-triazin-2-yl)morpholine (compound 1B11, Table 4, FIG. 2)

$^1$H NMR (400 MHz, CDCl$_3$) δ 8.34 (d, J=7.6 Hz, 1H), 7.88 (d, J=7.4 Hz, 1H), 7.65 (d, J=53.6 Hz, 1H), 7.46-7.34 (m, 2H), 7.18 (t, J=7.9 Hz, 1H), 6.77 (dd, J=13.9, 8.3 Hz, 3H), 4.60 (dd, J=6.0, 3.0 Hz, 1H), 4.13-3.98 (m, 2H), 3.88 (ddd, J=35.9, 18.7, 4.2 Hz, 10H), 2.34 (s, 3H), 1.96 (d, J=30.2 Hz, 4H). Mass: ESI [M+1]: 522.

4-(4-(2-(difluoromethyl)-1H-benzo[d]imidazol-1-yl)-6-(4-(o-tolyloxy)piperidin-1-yl)-1,3,5-triazin-2-yl)morpholine (compound 1B12, Table 4, FIG. 2)

$^1$H NMR (400 MHz, CDCl$_3$) δ 8.35 (d, J=7.4 Hz, 1H), 7.89 (d, J=7.2 Hz, 1H), 7.65 (d, J=53.6 Hz, 1H), 7.49-7.33 (m, 2H), 7.11 (d, J=8.4 Hz, 2H), 6.86 (d, J=8.5 Hz, 2H), 4.57 (dq, J=9.3, 3.2 Hz, 1H), 4.15-3.97 (m, 2H), 3.86 (ddd, J=37.4, 7.5, 4.1 Hz, 10H), 2.29 (d, J=14.1 Hz, 3H), 1.96 (dd, J=29.1, 3.9 Hz, 4H). Mass: ESI [M+1]:522.

4-(4-(5-fluoro-1H-benzo[d]imidazol-1-yl)-6-(4-(p-tolyloxy)piperidin-1-yl)-1,3,5-triazin-2-yl)morpholine (compound 1B13, Table 4, FIG. 2)

$^1$H NMR (400 MHz, CDCl$_3$) δ 8.19 (s, 1H), 7.79 (dd, J=7.5, 5.0 Hz, 1H), 7.43 (dd, J=8.0, 1.5 Hz, 1H), 7.13-7.04 (m, 3H), 6.82 (d, J=7.5 Hz, 2H), 4.42 (tt, J=7.8, 3.8 Hz, 1H), 3.79 (t, J=4.9 Hz, 4H), 3.55-3.41 (m, 6H), 3.32 (dt, J=12.4, 5.3 Hz, 2H), 2.31 (s, 3H), 2.30-2.19 (m, 2H), 2.01-1.90 (m, 2H) Mass: ESI [M+1]: 490.

4-(4-(5-fluoro-1H-benzo[d]imidazol-1-yl)-6-(4-(4-(trifluoromethyl)phenoxy)piperidin-1-yl)-1,3,5-triazin-2-yl)morpholine (compound 1B14, Table 4, FIG. 2)

$^1$H NMR (400 MHz, CDCl$_3$) δ 8.48 (s, 1H), 7.83 (dd, J=7.5, 5.0 Hz, 1H), 7.49 (dd, J=7.9, 1.5 Hz, 3H), 7.07 (td, J=7.8, 1.5 Hz, 1H), 6.88 (d, J=7.4 Hz, 2H), 4.41 (p, J=7.0 Hz, 1H), 3.79 (t, J=4.8 Hz, 4H), 3.58-3.41 (m, 6H), 3.39-3.28 (m, 2H), 2.29 (td, J=12.8, 6.0 Hz, 2H), 1.95 (td, J=12.8, 6.0 Hz, 2H) Mass: ESI [M+1]: 544.

4-(4-(1H-benzo[d]imidazol-1-yl)-6-(4-(4-(trifluoromethyl)phenoxy)piperidin-1-yl)-1,3,5-triazin-2-yl) morpholine (compound 1B15, Table 4, FIG. 2)

$^1$H NMR (400 MHz, CDCl$_3$) δ 8.46 (s, 1H), 8.14-7.76 (m, 1H), 7.74-7.61 (m, 1H), 7.49 (d, J=7.4 Hz, 2H), 7.37-7.23 (m, 2H), 6.88 (d, J=7.4 Hz, 2H), 4.41 (p, J=7.1 Hz, 1H), 3.79 (t, J=4.8 Hz, 4H), 3.58-3.41 (m, 6H), 3.33 (dt, J=12.1, 5.9 Hz, 2H), 2.29 (td, J=12.7, 5.9 Hz, 2H), 1.95 (td, J=12.6, 5.9 Hz, 2H) Mass: ESI [M+1]: 526.

4-(4-(1H-benzo[d]imidazol-1-yl)-6-(4-(4-(trifluoromethoxy)phenoxy)piperidin-1-yl)-1,3,5-triazin-2-yl)morpholine (compound 1B16, Table 4, FIG. 2)

$^1$H NMR (400 MHz, CDCl$_3$) δ 8.46 (s, 1H), 8.15-7.76 (m, 1H), 7.74-7.38 (m, 1H), 7.36-7.23 (m, 2H), 6.95-6.83 (m, 4H), 4.41 (p, J=7.0 Hz, 1H), 3.79 (t, J=4.8 Hz, 4H), 3.58-3.41 (m, 6H), 3.33 (dt, J=12.2, 5.9 Hz, 2H), 2.29 (td, J=12.7, 5.9 Hz, 2H), 1.95 (td, J=12.7, 5.9 Hz, 2H) Mass: ESI [M+1]: 542.

4-(4-(1H-benzo[d]imidazol-1-yl)-6-(4-(4-fluorophenoxy)piperidin-1-yl)-1,3,5-triazin-2-yl)morpholine (compound 1B17, Table 4, FIG. 2)

$^1$H NMR (400 MHz, CDCl$_3$) δ 8.14 (s, 1H), 8.13-7.73 (m, 1H), 7.69-7.52 (m, 1H), 7.29 (dtd, J=20.1, 7.4, 1.6 Hz, 2H), 6.97 (t, J=7.8 Hz, 2H), 6.91-6.80 (m, 2H), 4.45 (tt, J=7.8, 4.0 Hz, 1H), 3.78 (t, J=4.8 Hz, 4H), 3.57-3.40 (m, 6H), 3.33 (dt, J=12.4, 5.3 Hz, 2H), 2.28 (dqd, J=11.1, 5.4, 1.9 Hz, 2H), 1.97 (dqd, J=11.2, 5.5, 1.9 Hz, 2H) Mass: ESI [M+1]: 476.

4-(4-(1H-benzo[d]imidazol-1-yl)-6-(4-(2-fluorophenoxy)piperidin-1-yl)-1,3,5-triazin-2-yl)morpholine (compound 1B18, Table 4, FIG. 2)

$^1$H NMR (400 MHz, CDCl$_3$) δ 8.55-7.71 (m, 2H), 7.68-7.52 (m, 1H), 7.29 (dtd, J=19.3, 7.4, 1.6 Hz, 2H), 7.03-6.81 (m, 4H), 4.83 (tt, J=7.8, 3.9 Hz, 1H), 3.79 (t, J=4.9 Hz, 4H), 3.56-3.40 (m, 6H), 3.32 (dt, J=12.4, 5.3 Hz, 2H), 2.28 (dqd, J=11.1, 5.4, 1.8 Hz, 2H), 1.94 (dqd, J=11.1, 5.4, 1.8 Hz, 2H) Mass: ESI [M+1]: 476.

4-(4-(1H-benzo[d]imidazol-1-yl)-6-(4-(2-chlorophenoxy)piperidin-1yl)-1,3,5-triazin-2-yl)morpholine (compound 1B19, Table 4, FIG. 2)

$^1$H NMR (400 MHz, CDCl$_3$) δ 8.15 (s, 1H), 7.90-7.73 (m, 1H), 7.69-7.52 (m, 1H), 7.37-7.22 (m, 3H), 7.14 (td, J=7.5, 1.5 Hz, 1H), 7.09-6.31 (m, 2H), 4.71 (p, J=7.2 Hz, 1H), 3.78 (t, J=4.8 Hz, 4H), 3.57-3.40 (m, 6H), 3.33 (dt, J=12.2, 6.0 Hz, 2H), 2.28 (ddd, J=18.6, 10.1, 6.0 Hz, 2H), 1.96 (ddd, J=12.3, 10.1, 6.0 Hz, 2H) Mass: ESI [M+1]: 492.

4-(4-(1H-benzo[d]imidazol-1-yl)-6-(4-(2-(trifluoromethyl)phenoxy)piperidin-1-yl)-1,3,5-triazin-2-yl) morpholine (compound 1B20, Table 4, FIG. 2)

$^1$H NMR (400 MHz, CDCl$_3$) δ 8.47 (s, 1H), 8.14-7.76 (m, 1H), 7.74-7.62 (m, 1H), 7.54 (dd, J=7.5, 1.4 Hz, 1H), 7.37-7.23 (m, 3H), 7.05-6.93 (m, 2H), 4.25 (p, J=7.5 Hz, 1H), 3.79 (t, J=4.8 Hz, 4H), 3.58-3.42 (m, 6H), 3.20 (dt, J=12.3, 5.4 Hz, 2H), 2.36 (ddt, J=12.8, 7.4, 5.4 Hz, 2H), 2.00 (ddt, J=12.9, 7.5, 5.5 Hz, 2H) Mass: ESI [M+1]: 526.

1-(4-(2-(difluoromethyl)-1H-benzo[d]imidazol-1-yl)-6-morpholino-1,3,5-triazin-2-yl)-N-(4-fluoro phenyl)piperidin-4-amine (compound 1B21, Table 5, FIG. 3)

$^1$H NMR (400 MHz, CDCl$_3$) δ 8.34 (d, J=8.2 Hz, 1H), 7.89 (d, J=7.3 Hz, 1H), 7.65 (d, J=53.7 Hz, 1H), 7.41 (dt, J=13.7, 5.8 Hz, 2H), 6.92 (t, J=8.6 Hz, 2H), 6.75-6.50 (m, 2H), 4.69 (d, J=10.4 Hz, 2H), 3.84 (m, 8H), 3.64-3.44 (m, 1H), 3.33-3.03 (m, 1H), 2.20 (dd, J=12.2, 9.5 Hz, 2H), 1.45 (dd, J=21.1, 9.9 Hz, 2H). Mass: ESI [M+1]:525.

1-(4-(2-(difluoromethyl)-1H-benzo[d]imidazol-1-yl)-6-morpholino-1,3,5-triazin-2-yl)-N-(4-(trifluoromethyl)phenyl)piperidin-4-amine (compound 1B22, Table 5, FIG. 3)

$^1$H NMR (400 MHz, CDCl$_3$) δ 8.34 (d, J=8.8 Hz, 1H), 7.90 (d, J=8.3 Hz, 1H), 7.65 (d, J=53.7 Hz, 1H), 7.53-7.28 (m, 4H), 6.64 (d, J=8.6 Hz, 2H), 4.78-4.58 (m, 2H), 3.84 (dd, J=34.4, 4.2 Hz, 8H), 3.71-3.58 (m, 1H), 3.36-3.12 (m, 2H), 2.22 (td, J=10.7, 5.4 Hz, 2H), 1.51-1.35 (m, 2H). Mass: ESI [M+1]: 575.

1-(4-(2-(difluoromethyl)-1H-benzo[d]imidazol-1-yl)-6-morpholino-1,3,5-triazin-2-yl)-N-(4-(trifluoromethoxy)phenyl)piperidin-4-amine (compound 1B23, Table 5, FIG. 3)

$^1$H NMR (400 MHz, CDCl$_3$) δ 8.34 (d, J=7.4 Hz, 1H), 7.90 (d, J=7.2 Hz, 1H), 7.65 (d, J=53.7 Hz, 1H), 7.48-7.35 (m, 2H), 7.05 (d, J=8.5 Hz, 2H), 6.60 (d, J=8.9 Hz, 2H), 4.69 (d, J=9.2 Hz, 2H), 3.84 (dd, J=34.0, 3.7 Hz, 8H), 3.64-3.52 (m, 1H), 3.23 (dt, J=17.6, 7.5 Hz, 2H), 2.21 (t, J=11.4 Hz, 2H), 1.45 (dd, J=22.7, 11.7 Hz, 2H). Mass: ESI [M+1]:591.

1-(4-(2-(difluoromethyl)-1H-benzo[d]imidazol-1-yl)-6-morpholino-1,3,5-triazin-2-yl)-N-(4-methoxyphenyl)piperidin-4-amine (compound 1B24, Table 5, FIG. 3)

$^1$H NMR (400 MHz, CDCl$_3$) δ 8.34 (d, J=7.6 Hz, 1H), 7.89 (d, J=7.3 Hz, 1H), 7.65 (d, J=53.6 Hz, 1H), 7.48-7.33 (m, 2H), 6.80 (d, J=8.8 Hz, 2H), 6.65 (d, J=8.7 Hz, 2H), 4.79-4.53 (m, 2H), 3.88 (d, J=4.4 Hz, 4H), 3.80 (d, J=4.1 Hz, 4H), 3.76 (s, 3H), 3.55-3.48 (m, 1H), 3.21 (dt, J=23.5, 11.7 Hz, 2H), 2.18 (dd, J=14.8, 9.0 Hz, 2H), 1.46-1.37 (m, 2H). Mass: ESI [M+1]:537.

N-(4-bromophenyl)-1-(4-(2-(difluoromethyl)-1H-benzo[d]imidazol-1-yl)-6-morpholino-1,3,5-triazin-2-yl)piperidin-4-amine (compound 1B25, Table 5, FIG. 3)

$^1$H NMR (400 MHz, CDCl$_3$) δ 8.34 (d, J=8.4 Hz, 1H), 7.89 (d, J=8.3 Hz, 1H), 7.65 (d, J=53.6 Hz, 1H), 7.49-7.34 (m, 2H), 7.27 (d, J=7.5 Hz, 2H), 6.52 (d, J=8.8 Hz, 2H), 4.68 (d, J=10.5 Hz, 2H), 3.84 (dd, J=33.5, 3.9 Hz, 8H), 3.64-3.50 (m, 1H), 3.34-3.07 (m, 2H), 2.28-2.08 (m, 2H), 1.44 (dd, J=21.4, 10.4 Hz, 2H). Mass: ESI [M+1]:585.

N-(3,4-dichlorophenyl)-1-(4-(2-(difluoromethyl)-1H-benzo[d]imidazol-1-yl)-6-morpholino-1,3,5-triazin-2-yl)piperidin-4-amine (compound 1B26, Table 5, FIG. 3)

$^1$H NMR (400 MHz, CDCl$_3$) δ 8.34 (d, J=8.6 Hz, 1H), 7.90 (d, J=8.2 Hz, 1H), 7.65 (d, J=53.6 Hz, 1H), 7.48-7.35 (m, 2H), 7.20 (d, J=8.7 Hz, 1H), 6.71 (d, J=2.7 Hz, 1H), 6.46 (dd, J=8.7, 2.7 Hz, 1H), 4.69 (d, J=17.3 Hz, 2H), 3.84 (d, J=36.2 Hz, 8H), 3.55 (ddd, J=14.0, 9.9, 4.2 Hz, 1H), 3.21 (dd, J=14.7, 9.4 Hz, 2H), 2.26-2.11 (m, 2H), 1.47-1.38 (m, 2H). Mass: ESI [M+1]:575.

1-(4-(2-(difluoromethyl)-1H-benzo[d]imidazol-1-yl)-6-morpholino-1,3,5-triazin-2-yl)-N-(2-fluorophenyl)piperidin-4-amine (compound 1B27, Table 5, FIG. 3)

$^1$H NMR (400 MHz, CDCl$_3$) δ 8.34 (d, J=7.5 Hz, 1H), 7.89 (d, J=8.1 Hz, 1H), 7.65 (d, J=53.6 Hz, 1H), 7.41 (ddd, J=8.4, 7.1, 3.5 Hz, 2H), 7.06-6.94 (m, 2H), 6.77 (t, J=7.9 Hz, 1H), 6.71-6.59 (m, 1H), 4.67 (d, J=8.7 Hz, 2H), 3.84 (dd, J=33.4, 4.4 Hz, 8H), 3.70-3.55 (m, 1H), 3.36-3.15 (m, 2H), 2.21 (t, J=12.3 Hz, 2H), 1.50 (d, J=10.5 Hz, 2H). Mass: ESI [M+1]:525.

1-(4-(2-(difluoromethyl)-1H-benzo[d]imidazol-1-yl)-6-morpholino-1,3,5-triazin-2-yl)-N-(2-methoxyphenyl)piperidin-4-amine (compound 1B28, Table 5, FIG. 3)

$^1$H NMR (400 MHz, CDCl$_3$) δ 8.35 (d, J=8.4 Hz, 1H), 7.89 (d, J=8.4 Hz, 1H), 7.66 (d, J=53.6 Hz, 1H), 7.47-7.35 (m, 2H), 6.89 (td, J=7.8, 1.3 Hz, 1H), 6.79 (dd, J=8.2, 1.1 Hz, 1H), 6.69 (dd, J=10.1, 3.7 Hz, 2H), 4.63 (d, J=7.6 Hz, 2H), 3.88 (d, J=5.0 Hz, 4H), 3.84 (s, 3H), 3.80 (d, J=4.5 Hz, 4H), 3.68-3.55 (m, 1H), 3.29 (dt, J=23.5, 11.6 Hz, 2H), 2.30-2.09 (m, 2H), 1.58-1.44 (m, 2H). Mass: ESI [M+1]: 537.

1-(4-(2-(difluoromethyl)-1H-benzo[d]imidazol-1-yl)-6-morpholino-1,3,5-triazin-2-yl)-N-(2-(trifluoromethyl)phenyl)piperidin-4-amine (compound 1B29, Table 5, FIG. 3)

$^1$H NMR (400 MHz, CDCl$_3$) δ 8.34 (d, J=7.5 Hz, 1H), 7.89 (d, J=8.1 Hz, 1H), 7.65 (d, J=53.6 Hz, 1H), 7.41 (ddd, J=8.4, 7.1, 3.5 Hz, 2H), 7.06-6.94 (m, 2H), 6.92 (t, J=7.9 Hz, 1H), 6.71-6.59 (m, 1H), 4.67 (d, J=8.7 Hz, 2H), 3.84 (dd, J=33.4, 4.4 Hz, 8H), 3.70-3.55 (m, 1H), 3.36-3.15 (m, 2H), 2.21 (t, J=12.3 Hz, 2H), 1.50 (d, J=10.5 Hz, 2H). Mass: ESI [M+1]:575.

1-(4-(2-(difluoromethyl)-1H-benzo[d]imidazol-1-yl)-6-morpholino-1,3,5-triazin-2-yl)-N-(p-tolyl)piperidin-4-amine (compound 1B30, Table 5, FIG. 3)

$^1$H NMR (400 MHz, CDCl$_3$): δ 8.34 (d, J=7.4 Hz, 1H), 7.90 (d, J=7.2 Hz, 1H), 7.65 (t, J=53.7 Hz, 1H), 7.42 (m, 2H), 7.05 (d, J=8.5 Hz, 2H), 6.60 (d, J=8.9 Hz, 2H), 4.69 (d, J=17.1 Hz, 2H), 3.84 (dd, J=34.0, 3.7 Hz, 8H), 3.58 (m, 1H), 3.35-3.09 (m, 2H), 2.58 (s, 3H), 2.30-2.11 (m, 2H), 1.45 (dd, J=22.0, 9.8 Hz, 2H). Mass: ESI [M+1]: 522.

1-(4-(2-(difluoromethyl)-1H-benzo[d]imidazol-1-yl)-6-morpholino-1,3,5-triazin-2-yl)-N-(3-methoxyphenyl)piperidin-4-amine (compound 1B31, Table 6, FIG. 3)

$^1$H NMR (400 MHz, CDCl$_3$): δ 8.34 (d, J=7.4 Hz, 1H), 7.90 (d, J=7.2 Hz, 1H), 7.65 (t, J=53.7 Hz, 1H), 7.42 (m, 2H), 7.09 (s, 1H), 7.05 (d, J=6.5 Hz, 1H), 6.75 (d, J=8.9 Hz, 2H), 4.69 (d, J=17.1 Hz, 2H), 3.84 (dd, J=34.0, 3.7 Hz, 8H), 3.58 (m, 1H), 3.42 (s, 3H), 3.35-3.09 (m, 2H), 2.30-2.11 (m, 2H), 1.45 (dd, J=22.0, 9.8 Hz, 2H). Mass: ESI [M+1]: 537.

1-(4-(2-(difluoromethyl)-1H-benzo[d]imidazol-1-yl)-6-morpholino-1,3,5-triazin-2-yl)-N-(o-tolyl)piperidin-4-amine (compound 1B32, Table 6, FIG. 3)

$^1$H NMR (400 MHz, CDCl$_3$): δ 8.34 (d, J=7.4 Hz, 1H), 7.90 (d, J=7.2 Hz, 1H), 7.65 (t, J=53.7 Hz, 1H), 7.42 (m, 2H), 7.15 (d, J=8.5 Hz, 1H), 7.05 (d, J=6.5 Hz, 1H), 6.60 (d, J=8.9 Hz, 2H), 4.69 (d, J=17.1 Hz, 2H), 3.84 (dd, J=34.0, 3.7 Hz, 8H), 3.58 (m, 1H), 3.35-3.09 (m, 2H), 2.43 (s, 3H), 2.30-2.11 (m, 2H), 1.45 (dd, J=22.0, 9.8 Hz, 2H). Mass: ESI [M+1]: 521.

1-(4-(5-fluoro-1H-benzo[d]imidazol-1-yl)-6-morpholino-1,3,5-triazin-2-yl)-N-(p-tolyl)piperidin-4-amine (compound 1B33, Table 6, FIG. 3)

$^1$H NMR (400 MHz, CDCl$_3$) δ 8.48 (s, 1H), 7.82 (dd, J=7.5, 5.0 Hz, 1H), 7.49 (dd, J=8.0, 1.5 Hz, 1H), 7.11-6.96 (m, 3H), 6.50 (d, J=7.4 Hz, 2H), 3.80 (dd, J=13.9, 9.2 Hz, 5H), 3.53 (dddd, J=20.4, 14.8, 7.8, 3.9 Hz, 7H), 3.29 (dt, J=12.3, 5.6 Hz, 2H), 2.30 (s, 3H), 1.92 (dtd, J=12.2, 5.6, 3.1 Hz, 2H), 1.79 (dtd, J=12.4, 5.6, 3.1 Hz, 2H) Mass: ESI [M+1]: 489.

1-(4-(2-(difluoromethyl)-5-fluoro-1H-benzo[d]imidazol-1-yl)-6-morpholino-1,3,5-triazin-2-yl)-N-(4-(trifluoromethyl)phenyl)piperidin-4-amine (compound 1B34, Table 6, FIG. 3)

$^1$H NMR (400 MHz, CDCl$_3$) δ 8.47 (s, 1H), 7.81 (dd, J=7.5, 5.0 Hz, 1H), 7.53-7.39 (m, 3H), 7.07 (td, J=7.8, 1.4 Hz, 1H), 6.63 (d, J=7.4 Hz, 2H), 3.79 (t, J=4.8 Hz, 4H), 3.63-3.41 (m, 7H), 3.13 (dt, J=12.3, 5.6 Hz, 2H), 1.90 (dtd, J=12.3, 5.6, 3.9 Hz, 2H), 1.78 (dtd, J=12.4, 5.6, 3.9 Hz, 2H), 0.36 (s, 1H) Mass: ESI [M+1]: 543.

1-(4-(1H-benzo[d]imidazol-1-yl)-6-morpholino-1,3,5-triazin-2-yl)-N-(4-(trifluoromethyl)phenyl)piperidin-4-amine (compound 1B35, Table 6, FIG. 3)

$^1$H NMR (400 MHz, CDCl$_3$) δ 8.45 (s, 1H), 8.18-7.75 (m, 1H), 7.74-7.48 (m, 1H), 7.43 (d, J=7.6 Hz, 2H), 7.30 (pd, J=7.5, 1.7 Hz, 2H), 6.63 (d, J=7.4 Hz, 2H), 3.79 (t, J=4.8 Hz, 4H), 3.63-3.41 (m, 7H), 3.13 (dt, J=12.4, 5.6 Hz, 2H), 1.90

(dtd, J=12.3, 5.6, 3.9 Hz, 2H), 1.78 (dtd, J=12.3, 5.6, 3.8 Hz, 2H), 0.37 (s, 1H) Mass: ESI [M+1]: 525.

1-(4-(1H-benzo[d]imidazol-1-yl)-6-morpholino-1,3, 5-triazin-2-yl)-N-(4-(trifluoromethoxy)phenyl)piperidin-4-amine (compound 1B36, Table 6, FIG. 3)

$^1$H NMR (400 MHz, CDCl$_3$) δ 8.18 (s, 1H), 8.15-7.72 (m, 1H), 7.68-7.52 (m, 1H), 7.29 (dtd, J=19.6, 7.4, 1.7 Hz, 2H), 6.77 (d, J=7.4 Hz, 2H), 6.50 (d, J=7.4 Hz, 2H), 3.95 (s, 1H), 3.79 (t, J=4.9 Hz, 4H), 3.61-3.42 (m, 7H), 3.29 (dt, J=12.5, 6.3 Hz, 2H), 1.97-1.74 (m, 4H) Mass: ESI [M+1]: 541.

1-(4-(1H-benzo[d]imidazol-1-yl)-6-morpholino-1,3, 5-triazin-2-yl)-N-(4-fluorophenyl)piperidin-4-amine (compound 1B37, Table 6, FIG. 3)

$^1$H NMR (400 MHz, CDCl$_3$) δ 8.14 (s, 1H), 8.14-7.73 (m, 1H), 7.68-7.52 (m, 1H), 7.29 (dtd, J=19.5, 7.4, 1.6 Hz, 2H), 6.86 (t, J=7.7 Hz, 2H), 6.58-6.46 (m, 2H), 3.78 (t, J=4.9 Hz, 4H), 3.58-3.27 (m, 10H), 1.97 (ddt, J=12.2, 7.4, 6.0 Hz, 2H), 1.81 (ddt, J=12.3, 7.5, 6.1 Hz, 2H) Mass: ESI [M+1]: 475.

1-(4-(1H-benzo[d]imidazol-1-yl)-6-morpholino-1,3, 5-triazin-2-yl)-N-(2-fluorophenyl)piperidin-4-amine (compound 1B38, Table 6, FIG. 3)

$^1$H NMR (400 MHz, CDCl$_3$) δ 8.17 (s, 1H), 8.15-7.71 (m, 1H), 7.68-7.52 (m, 1H), 7.29 (dtd, J=19.5, 7.4, 1.6 Hz, 2H), 6.93-6.80 (m, 2H), 6.69-6.51 (m, 2H), 4.00 (s, 1H), 3.79 (t, J=4.9 Hz, 4H), 3.57-3.38 (m, 7H), 3.36-3.25 (m, 2H), 2.06-1.93 (m, 2H), 1.91-1.79 (m, 2H) Mass: ESI [M+1]: 475.

1-(4-(1H-benzo[d]imidazol-1-yl)-6-morpholino-1,3, 5-triazin-2-yl)-N-(2-chlorophenyl)piperidin-4-amine (compound 1B39, Table 6, FIG. 3)

$^1$H NMR (400 MHz, CDCl$_3$) δ 8.60-7.71 (m, 2H), 7.68-7.52 (m, 1H), 7.29 (dtd, J=19.5, 7.4, 1.6 Hz, 2H), 7.14 (dd, J=7.5, 1.4 Hz, 1H), 7.02 (td, J=7.5, 1.4 Hz, 1H), 6.64-6.51 (m, 2H), 4.64 (s, 1H), 3.79 (t, J=4.9 Hz, 4H), 3.57-3.41 (m, 7H), 3.36-3.25 (m, 2H), 2.06-1.93 (m, 2H), 1.91-1.78 (m, 2H) Mass: ESI [M+1]: 491.

1-(4-(1H-benzo[d]imidazol-1-yl)-6-morpholino-1,3, 5-triazin-2-yl)-N-(2-(trifluoromethyl)phenyl)piperidin-4-amine (compound 1B40, Table 6, FIG. 3)

$^1$H NMR (400 MHz, CDCl$_3$) δ 8.47 (s, 5H), 8.18-7.76 (m, 5H), 7.74-7.33 (m, 11H), 7.33 (d, J=1.9 Hz, 1H), 7.36-7.23 (m, 10H), 7.18 (td, J=7.5, 1.4 Hz, 5H), 6.65 (td, J=7.5, 1.5 Hz, 5H), 6.56 (dd, J=7.5, 1.5 Hz, 5H), 4.82 (s, 5H), 3.78 (t, J=4.5 Hz, 20H), 3.59-3.29 (m, 45H), 2.11-1.98 (m, 10H), 1.77-1.63 (m, 10H) Mass: ESI [M+1]: 525.

Figure 4:
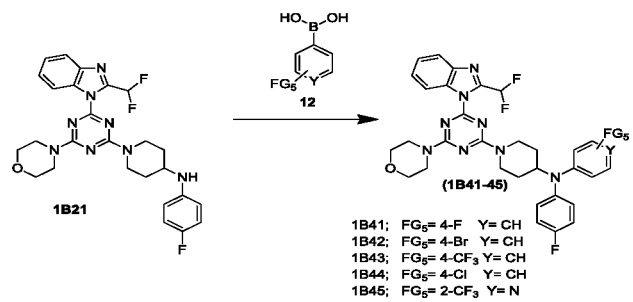
FIG. 4 shows the synthetic approach (scheme4) for the synthesis of compounds 1B (41-45).

1-(4-(2-(difluoromethyl)-1H-benzo[d]imidazol-1-yl)-6-morpholino-1,3,5-triazin-2-yl)-N,N-bis(4-fluorophenyl)piperidin-4-amine (compound 1B41, Table 7, FIG. 4)

$^1$H NMR (400 MHz, CDCl$_3$) δ 7.78 (dt, J=14.5, 7.2 Hz, 1H), 7.59 (dd, J=7.3, 1.8 Hz, 1H), 7.33-7.20 (m, 2H), 7.07 (d, J=40.9 Hz, 1H), 7.05-6.87 (m, 8H), 4.02 (tt, J=8.0, 5.0 Hz, 1H), 3.78 (t, J=4.8 Hz, 4H), 3.54 (t, J=4.9 Hz, 2H), 3.49-3.37 (m, 4H), 3.31 (dt, J=12.4, 5.3 Hz, 2H), 2.26-2.15 (m, 2H), 1.88-1.75 (m, 2H). Mass: ESI [M+1]: 619

N-(4-bromophenyl)-1-(4-(2-(difluoromethyl)-1H-benzo[d]imidazol-1-yl)-6-morpholino-1,3,5-triazin-2-yl)-N-(4-fluorophenyl)piperidin-4-amine (compound 1B42, Table 7, FIG. 4)

$^1$H NMR (400 MHz, CDCl$_3$) δ 7.80 (dd, J=6.9, 2.1 Hz, 1H), 7.65 (dd, J=6.9, 2.2 Hz, 1H), 7.34 (d, J=7.6 Hz, 2H), 7.31-7.21 (m, 2H), 7.14-7.06 (m, 3H), 6.96 (t, J=7.7 Hz, 2H), 6.84 (d, J=7.4 Hz, 2H), 4.19 (p, J=3.7 Hz, 1H), 3.79 (t, J=4.8 Hz, 4H), 3.52 (ddt, J=22.1, 9.5, 5.2 Hz, 6H), 3.21-3.07 (m, 2H), 2.09 (dtdd, J=18.2, 12.3, 5.7, 3.7 Hz, 4H) Mass: ESI [M+1]: 679

1-(4-(2-(difluoromethyl)-1H-benzo[d]imidazol-1-yl)-6-morpholino-1,3,5-triazin-2-yl)-N-(4-fluorophenyl)-N-(4-(trifluoromethyl)phenyl)piperidin-4-amine (compound 1B43, Table 7, FIG. 4)

$^1$H NMR (400 MHz, CDCl$_3$) δ 7.85-7.74 (m, 1H), 7.70-7.58 (m, 1H), 7.48 (d, J=7.6 Hz, 2H), 7.33-7.21 (m, 2H), 7.12 (dd, J=7.7, 4.1 Hz, 5H), 7.02-6.89 (m, 2H), 4.14 (p, J=3.1 Hz, 1H), 3.78 (t, J=4.5 Hz, 4H), 3.64-3.47 (m, 4H), 3.41 (t, J=4.5 Hz, 2H), 3.25 (dt, J=12.4, 5.3 Hz, 2H), 1.98 (dtd, J=12.4, 5.3, 3.1 Hz, 2H), 1.83 (dtd, J=12.4, 5.3, 3.1 Hz, 2H). ESI [M+1]: 669

N-(4-chlorophenyl)-1-(4-(2-(difluoromethyl)-1H-benzo[d]imidazol-1-yl)-6-morpholino-1,3,5-triazin-2-yl)-N-(4-fluorophenyl)piperidin-4-amine (compound 1B44, Table 7, FIG. 4)

$^1$H NMR (400 MHz, CDCl$_3$) δ 7.76 (dd, J=7.3, 1.6 Hz, 1H), 7.59 (dd, J=7.3, 1.8 Hz, 1H), 7.26 (dqd, J=14.5, 7.4, 1.6 Hz, 2H), 7.18 (d, J=7.4 Hz, 2H), 7.12 (t, J=12, 2H), 7.10-7.05 (m, 2H), 6.96 (t, J=7.7 Hz, 2H), 6.88 (d, J=7.6 Hz, 2H), 3.98 (tt, J=8.1, 5.1 Hz, 1H), 3.78 (t, J=4.9 Hz, 4H), 3.51 (t, J=4.9 Hz, 2H), 3.47-3.39 (m, 4H), 3.30 (dt, J=12.4, 5.4 Hz, 2H), 2.22-2.11 (m, 2H), 1.84-1.73 (m, 2H). ESI [M+1]: 635

N-(1-(4-(2-(difluoromethyl)-1H-benzo[d]imidazol-1-yl)-6-morpholino-1,3,5-triazin-2-yl)piperidin-4-yl)-N-(4-fluorophenyl)-3-(trifluoromethyl)pyridin-4-amine (compound 1B45, Table 7, FIG. 4)

$^1$H NMR (400 MHz, CDCl$_3$) δ 9.24 (s, 4H), 8.80 (d, J=7.5 Hz, 4H), 7.89-7.77 (m, 4H), 7.65 (ddd, J=20.2, 14.0, 6.4 Hz, 8H), 7.36-7.21 (m, 9H), 7.12 (s, 2H), 6.96 (ddd, J=26.8, 11.5, 6.4 Hz, 17H), 4.41 (p, J=7.5 Hz, 4H), 3.78 (t, J=4.5 Hz, 14H), 3.62 (t, J=4.5 Hz, 8H), 3.40 (tdt, J=24.2, 12.2, 6.0 Hz, 24H), 2.22 (ddt, J=12.2, 7.4, 6.0 Hz, 8H), 2.10-1.92 (m, 8H). ESI [M+1]: 670

Figure 5:
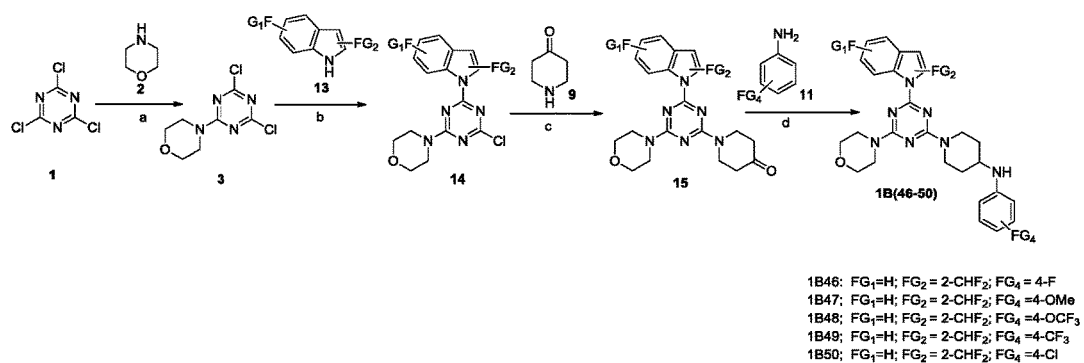
FIG. 5 shows the synthetic approach (scheme6) for the synthesis of compounds 1B (46-50).
Table 1 shows the structures of representative compounds IA (1-10) belong to formula IA and synthesized as per scheme 1 provided in (FIG. 1).
Table 2 shows the structures of representative compounds IA (10-20) belong to formula IA and synthesized as per scheme 1 provided in (FIG. 1).
Table 3 shows the structures of representative compounds IB (1-10) belong to formula IB and synthesized as per scheme 2 provided in (FIG. 2).
Table 4 shows the structures of representative compounds IB (10-20) belong to formula IB and synthesized as per scheme 2 provided in (FIG. 2).
Table 5 shows the structures of representative compounds IB (21-30) belong to formula IB and synthesized as per scheme 3 provided in (FIG. 3).
Table 6 shows the structures of representative compounds IB (31-40) belong to formula IB and synthesized as per scheme 3 provided in (FIG. 3).
Table 7 shows the structures of representative compounds IB (40-50) belong to formula IB and synthesized as per scheme 4 and scheme 5 provided in (FIG. 4 & FIG. 5).
Table 8 shows the inhibition results of compounds general formula 1 by enzyme based assay PI3Kα. *In vitro PI3K alpha kinase inhibition at 500 nm; + indicates greater than 50% to 70% of inhibition and ++ indicates greater than 70% of inhibition.
Table 9 shows the inhibition results of compounds of general formula 1 by MTT assay on cancer cell line *In vitro cell line inhibition at 10 μM: + indicates 30% to 50% of inhibition and ++ indicates greater than 50% of inhibition.

1-(4-(2-(difluoromethyl)-1H-indol-1-yl)-6-morpholino-1,3,5-triazin-2-yl)-N-(4-fluorophenyl)piperidin-4-amine (compound 1B46, Table 7, FIG. 5)

$^1$H NMR (400 MHz, CDCl$_3$) δ 7.49-7.40 (m, 1H), 7.33-7.24 (m, 1H), 7.23-7.13 (m, 2H), 7.07 (dd, J=29.4, 28.0 Hz, 2H), 6.87 (t, J=7.8 Hz, 2H), 6.57-6.47 (m, 2H), 4.25 (s, 1H), 3.78 (t, J=4.5 Hz, 4H), 3.59-3.46 (m, 5H), 3.42 (t, J=4.5 Hz, 2H), 3.19 (dt, J=12.4, 5.4 Hz, 2H), 1.99 (dtd, J=12.4, 5.4, 3.2 Hz, 2H), 1.71 (dtd, J=12.4, 5.5, 3.2 Hz, 2H). ESI [M+1]:524

1-(4-(2-(difluoromethyl)-1H-indol-1-yl)-6-morpholino-1,3,5-triazin-2-yl)-N-(4-methoxyphenyl)piperidin-4-amine (compound 1B47, Table 7, FIG. 5)

¹H NMR (400 MHz, CDCl₃) δ 7.48-7.37 (m, 1H), 7.32-7.24 (m, 1H), 7.22-7.13 (m, 2H), 7.06 (dd, J=29.4, 28.0 Hz, 2H), 6.75 (d, J=7.4 Hz, 2H), 6.52 (d, J=7.4 Hz, 2H), 3.79 (dd, J=9.3, 4.8 Hz, 7H), 3.64 (s, 1H), 3.60-3.46 (m, 5H), 3.42 (t, J=4.5 Hz, 2H), 3.25 (dt, J=12.4, 5.5 Hz, 2H), 1.90 (dtd, J=12.3, 5.4, 3.2 Hz, 2H), 1.71 (dtd, J=12.4, 5.5, 3.2 Hz, 2H). ESI [M+1]: 536

1-(4-(2-(difluoromethyl)-1H-indol-1-yl)-6-morpholino-1,3,5-triazin-2-yl)-N-(4-(trifluoromethoxy)phenyl)piperidin-4-amine (compound 1B48, Table 7, FIG. 5)

¹H NMR (400 MHz, CDCl₃) δ 7.44-7.36 (m, 1H), 7.28-7.22 (m, 1H), 7.18 (ddd, J=14.9, 7.2, 1.7 Hz, 2H), 7.13-6.96 (m, 2H), 6.76 (d, J=7.4 Hz, 2H), 6.51 (d, J=7.4 Hz, 2H), 3.79 (t, J=4.9 Hz, 4H), 3.58-3.40 (m, 7H), 3.31 (p, J=7.5 Hz, 1H), 3.20 (dt, J=12.3, 5.5 Hz, 2H), 2.00 (ddt, J=13.0, 7.6, 5.6 Hz, 2H), 1.81 (ddt, J=13.0, 7.5, 5.5 Hz, 2H). ESI [M+1]: 590

1-(4-(2-(difluoromethyl)-1H-indol-1-yl)-6-morpholino-1,3,5-triazin-2-yl)-N-(4-(trifluoromethyl)phenyl)piperidin-4-amine (compound 1B49, Table 7, FIG. 5)

¹H NMR (400 MHz, CDCl₃) δ 7.50-7.42 (m, 1H), 7.38 (d, J=7.4 Hz, 2H), 7.27-7.13 (m, 3H), 7.07 (dd, J=44.8, 14.7 Hz, 1H), 6.97 (d, J=1.4 Hz, 1H), 6.52 (d, J=7.4 Hz, 2H), 4.02 (s, 1H), 3.78 (t, J=4.9 Hz, 4H), 3.61 (t, J=4.9 Hz, 2H), 3.52-3.39 (m, 5H), 3.32 (dt, J=12.3, 5.3 Hz, 2H), 2.03-1.92 (m, 2H), 1.86-1.75 (m, 2H). ESI [M+1]: 574

N-(4-chlorophenyl)-1-(4-(2-(difluoromethyl)-1H-indol-1-yl)-6-morpholino-1,3,5-triazin-2-yl)piperidin-4-amine (compound 1B50, Table 7, FIG. 5)

¹H NMR (400 MHz, CDCl₃) δ 7.45 (dd, J=7.1, 1.8 Hz, 1H), 7.30-7.25 (m, 1H), 7.18 (ddt, J=7.8, 5.7, 1.6 Hz, 4H), 7.06 (dd, J=29.4, 28.0 Hz, 2H), 6.49 (d, J=7.4 Hz, 2H), 4.06 (s, 1H), 3.78 (t, J=4.5 Hz, 4H), 3.59-3.46 (m, 5H), 3.42 (t, J=4.5 Hz, 2H), 3.24 (dt, J=12.4, 5.4 Hz, 2H), 1.89 (dtd, J=12.4, 5.4, 3.2 Hz, 2H), 1.70 (dtd, J=12.4, 5.4, 3.2 Hz, 2H). ESI [M+1]: 540

TABLE 1

| Entry | Code | Structure |
|---|---|---|
| 1. | 1A1 | (structure) |
| 2. | 1A2 | (structure) |
| 3. | 1A3 | (structure) |
| 4. | 1A4 | (structure) |

TABLE 1-continued
| Entry | Code | Structure |
|---|---|---|
| 5. | 1A5 | 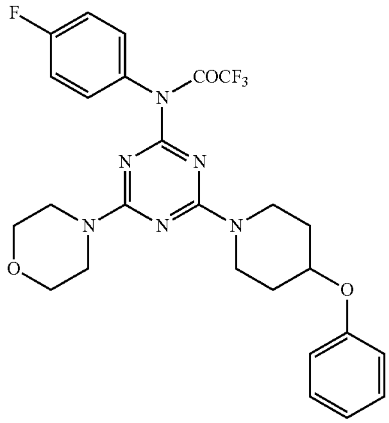 |
| 6. | 1A6 | 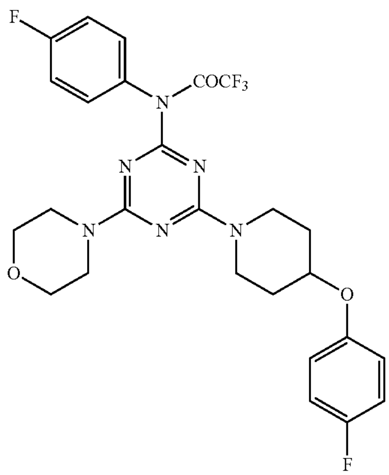 |
| 7. | 1A7 | 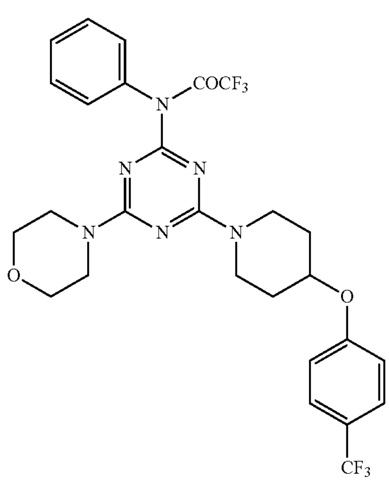 |
| 8. | 1A8 | 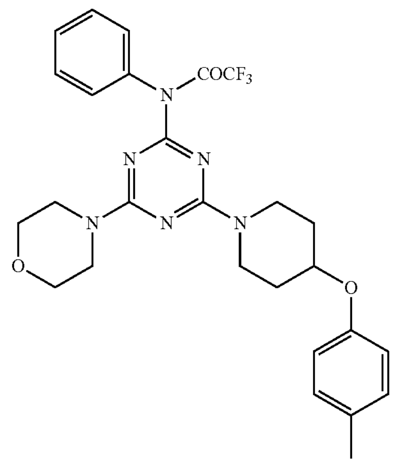 |
| 9. | 1A9 | 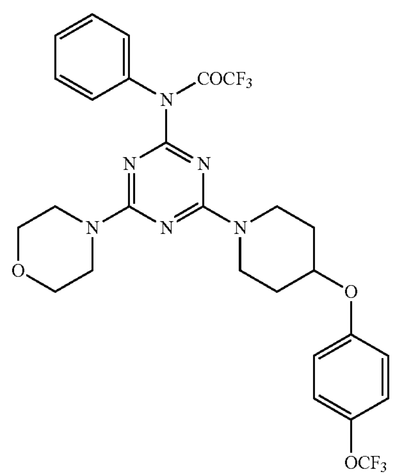 |
| 10. | 1A10 | 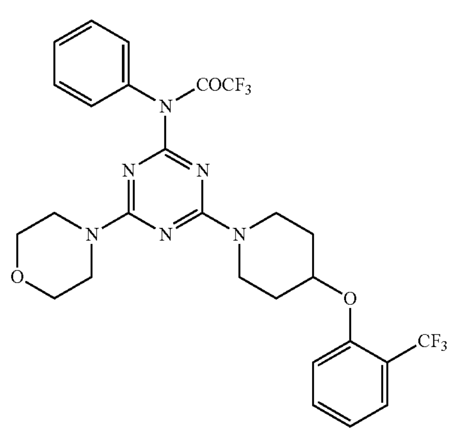 |
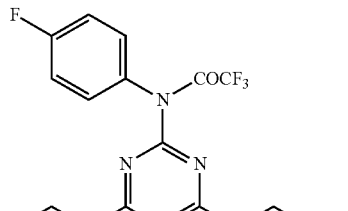

TABLE 2
| Entry | Code | Structure |
|---|---|---|
| 11 | 1A11 | 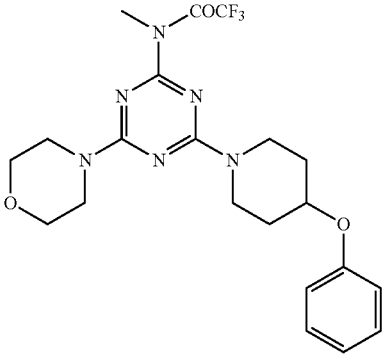 |
| 12 | 1A12 | 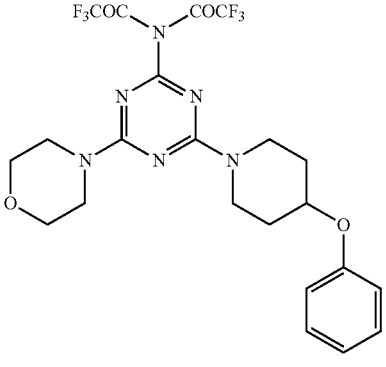 |
| 13 | 1A13 | 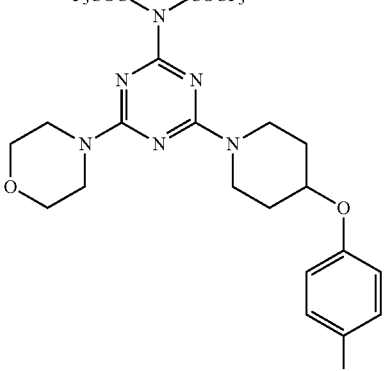 |
| 14 | 1A14 | 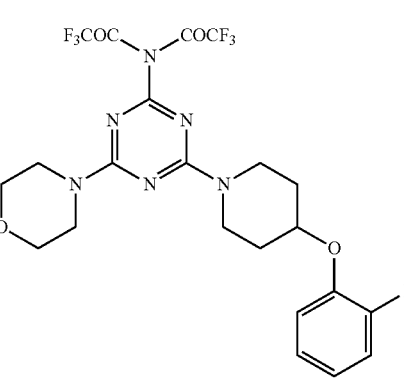 |
| 15 | 1A15 | 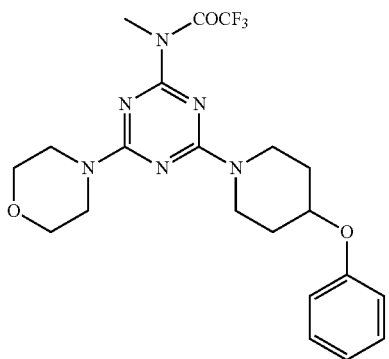 |
| 16 | 1A16 | 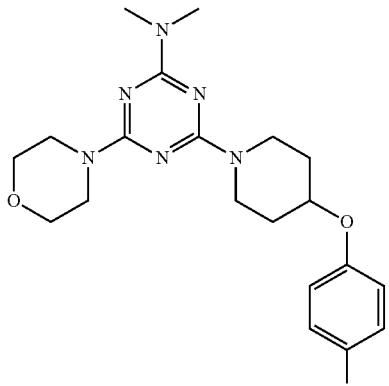 |
| 17 | 1A17 |  |

TABLE 2-continued
| Entry | Code | Structure |
|---|---|---|
| 18 | 1A18 | 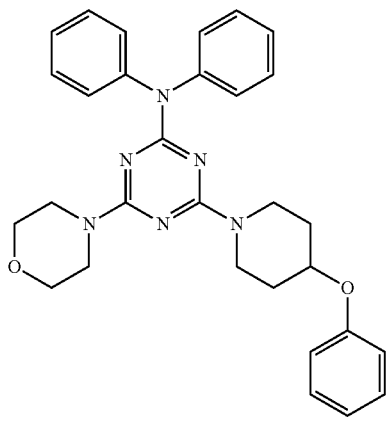 [SMILES: c1ccc(OC2CCN(c3nc(N4CCOCC4)nc(N(c4ccccc4)c4ccccc4)n3)CC2)cc1] |
| 19 | 1A19 | 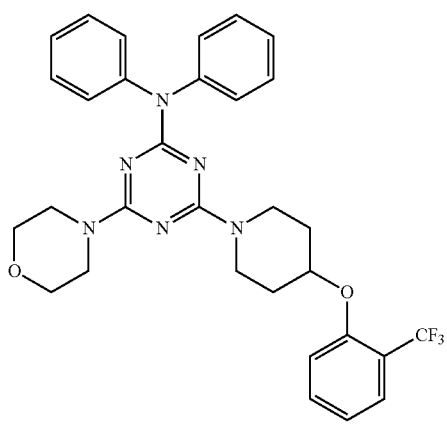 [SMILES: FC(F)(F)c1ccccc1OC1CCN(c2nc(N3CCOCC3)nc(N(c3ccccc3)c3ccccc3)n2)CC1] |
| 20 | 1A20 | 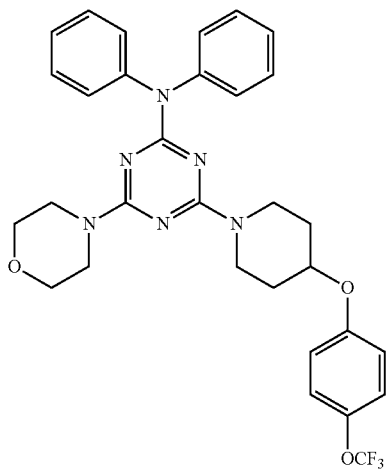 [SMILES: FC(F)(F)Oc1ccc(OC2CCN(c3nc(N4CCOCC4)nc(N(c4ccccc4)c4ccccc4)n3)CC2)cc1] |
TABLE 3
| Entry | Code | Structure |
|---|---|---|
| 21 | 1B1 | 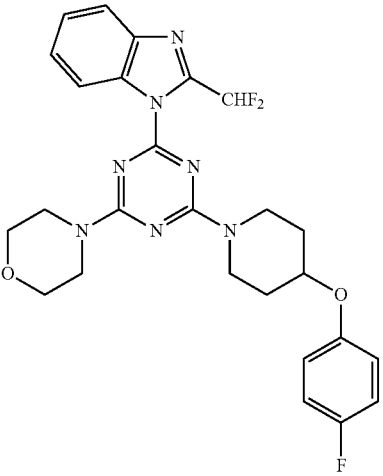 [SMILES: Fc1ccc(OC2CCN(c3nc(N4CCOCC4)nc(-n4c(C(F)F)nc5ccccc54)n3)CC2)cc1] |
| 22 | 1B2 | 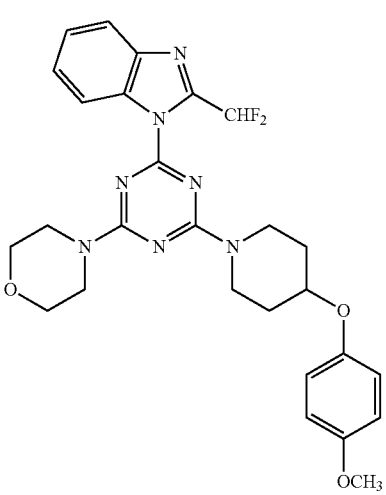 [SMILES: COc1ccc(OC2CCN(c3nc(N4CCOCC4)nc(-n4c(C(F)F)nc5ccccc54)n3)CC2)cc1] |
| 23 | 1B3 | 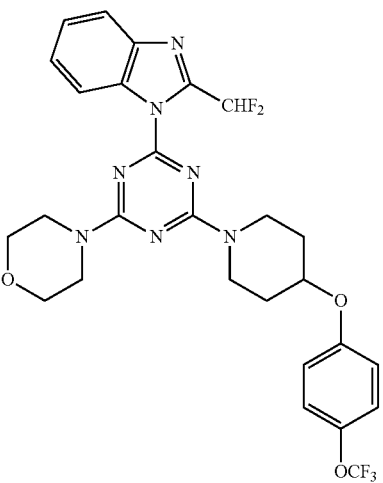 [SMILES: FC(F)c1nc2ccccc2n1-c1nc(N2CCOCC2)nc(N2CCC(Oc3ccc(OC(F)(F)F)cc3)CC2)n1] |

TABLE 3-continued

| Entry | Code | Structure |
|---|---|---|
| 24 | 1B4 | 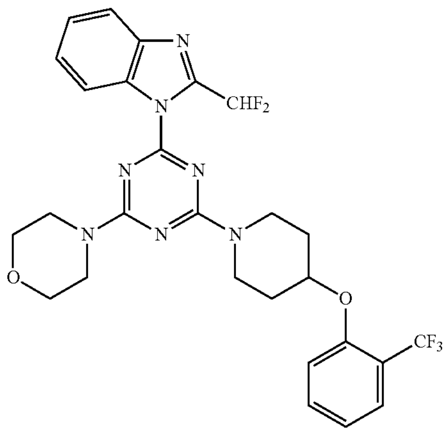 [SMILES: FC(F)c1nc2ccccc2n1-c1nc(N2CCOCC2)nc(N2CCC(Oc3ccccc3C(F)(F)F)CC2)n1] |
| 25 | 1B5 | 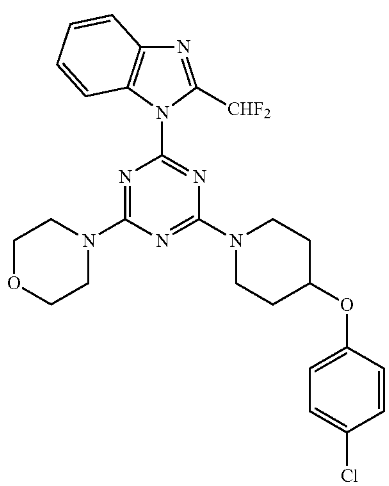 [SMILES: FC(F)c1nc2ccccc2n1-c1nc(N2CCOCC2)nc(N2CCC(Oc3ccc(Cl)cc3)CC2)n1] |
| 26 | 1B6 | 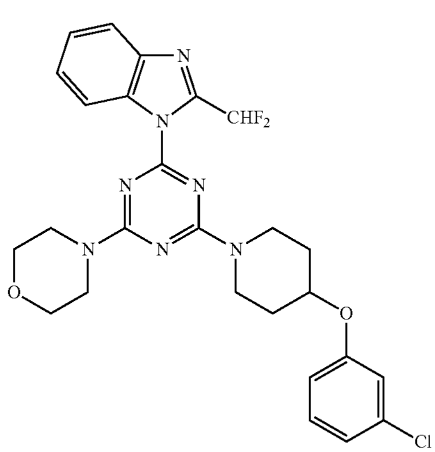 [SMILES: FC(F)c1nc2ccccc2n1-c1nc(N2CCOCC2)nc(N2CCC(Oc3cccc(Cl)c3)CC2)n1] |
| 27 | 1B7 | |
| 28 | 1B8 | |
| 29 | 1B9 | |

TABLE 3-continued
| Entry | Code | Structure |
|---|---|---|
| 30 | 1B10 | 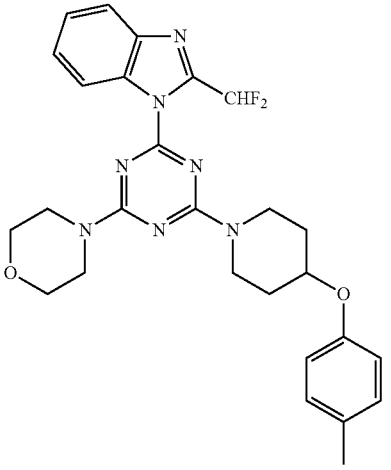 [SMILES: Cc1ccc(OC2CCN(c3nc(N4CCOCC4)nc(-n4c(C(F)F)nc5ccccc54)n3)CC2)cc1] |
TABLE 4
| Entry | Code | Structure |
|---|---|---|
| 31 | 1B11 | 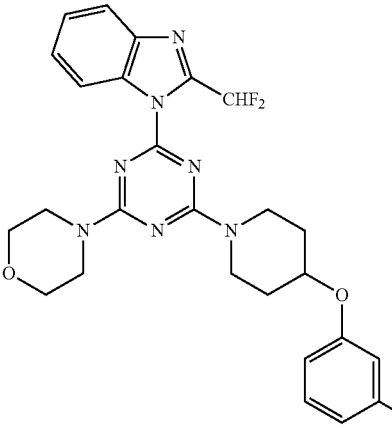 |
| 32 | 1B12 | 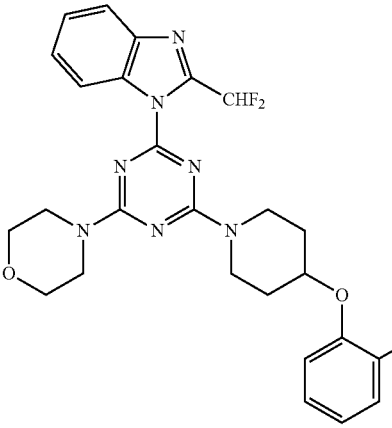 |
TABLE 4-continued
| Entry | Code | Structure |
|---|---|---|
| 33 | 1B13 | 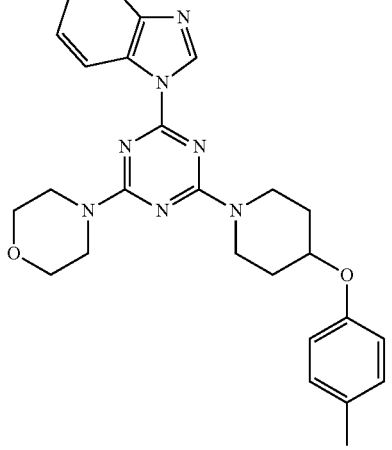 |
| 34 | 1B14 | 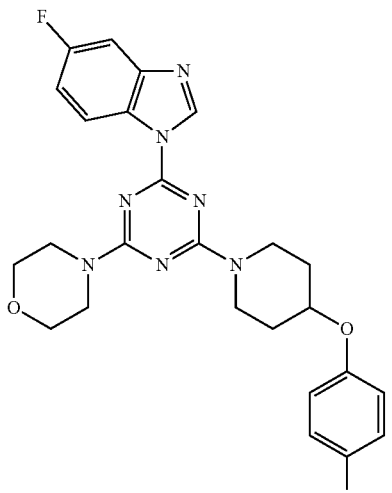 |
| 35 | 1B15 | 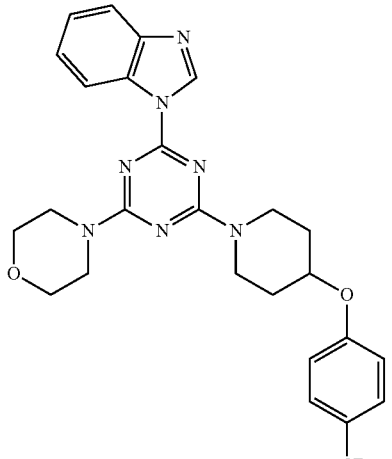 |

TABLE 4-continued

| Entry | Code | Structure |
|---|---|---|
| 36 | 1B16 | 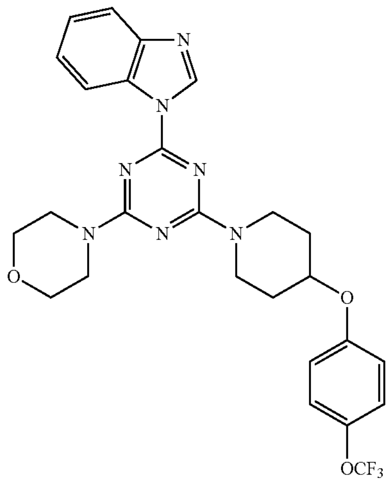 [SMILES: FC(F)(F)Oc1ccc(OC2CCN(c3nc(N4CCOCC4)nc(-n4cnc5ccccc54)n3)CC2)cc1] |
| 37 | 1B17 | 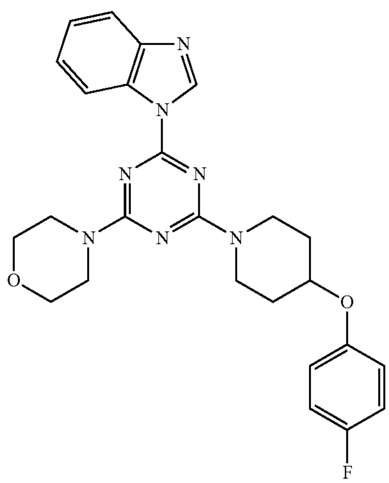 [SMILES: Fc1ccc(OC2CCN(c3nc(N4CCOCC4)nc(-n4cnc5ccccc54)n3)CC2)cc1] |
| 38 | 1B18 | 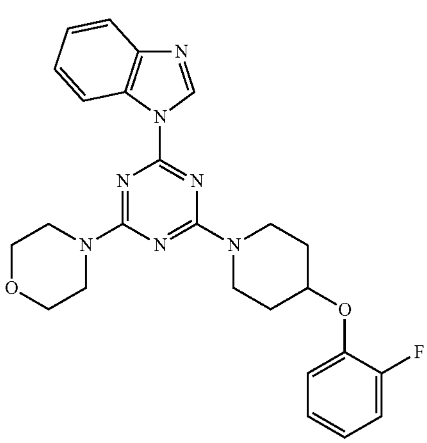 [SMILES: Fc1ccccc1OC1CCN(c2nc(N3CCOCC3)nc(-n3cnc4ccccc43)n2)CC1] |
| 39 | 1B19 | |
| 40 | 1B20 | |

TABLE 5

| Entry | Code | Structure |
|---|---|---|
| 41. | 1B21 | 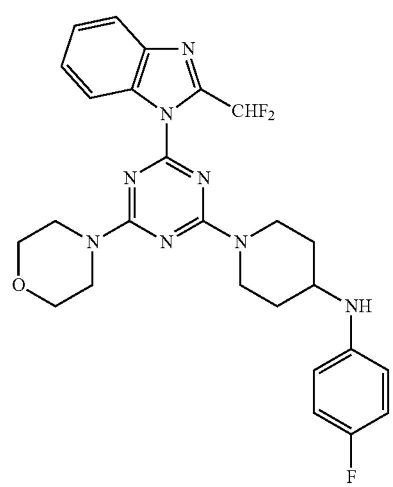 [SMILES: Fc1ccc(NC2CCN(c3nc(N4CCOCC4)nc(-n4c(C(F)F)nc5ccccc54)n3)CC2)cc1] |

TABLE 5-continued

| Entry Code | Structure |
|---|---|
| 42. 1B22 | benzimidazole-CHF2 / triazine / morpholine / piperidine-NH-phenyl-CF3 |
| 43. 1B23 | benzimidazole-CHF2 / triazine / morpholine / piperidine-NH-phenyl-OCF3 |
| 44. 1B24 | benzimidazole-CHF2 / triazine / morpholine / piperidine-NH-phenyl-OCH3 |
| 45. 1B25 | benzimidazole-CHF2 / triazine / morpholine / piperidine-NH-phenyl-Br |
| 46. 1B26 | benzimidazole-CHF2 / triazine / morpholine / piperidine-NH-phenyl-3,4-diCl |
| 47. 1B27 | benzimidazole-CHF2 / triazine / morpholine / piperidine-NH-phenyl-2-F |

TABLE 5-continued

| Entry | Code | Structure |
|---|---|---|
| 48. | 1B28 | (structure) |
| 49. | 1B29 | (structure) |
| 50. | 1B30 | (structure) |

TABLE 6

| Entry | Code | Structure |
|---|---|---|
| 51 | 1B31 | (structure) |
| 52 | 1B32 | (structure) |
| 53 | 1B33 | (structure) |

TABLE 6-continued
| Entry | Code | Structure |
|---|---|---|
| 54 | 1B34 | 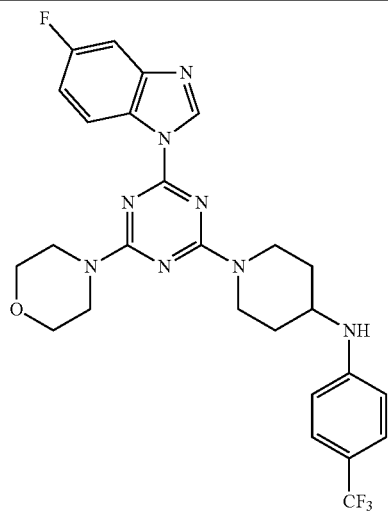 |
| 55 | 1B35 | 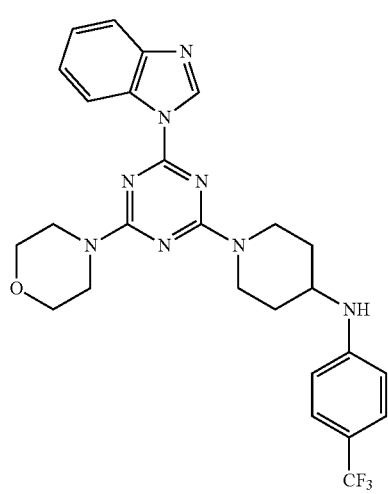 [SMILES: FC(F)(F)c1ccc(NC2CCN(c3nc(N4CCOCC4)nc(-n4cnc5ccccc54)n3)CC2)cc1] |
| 56 | 1B36 | 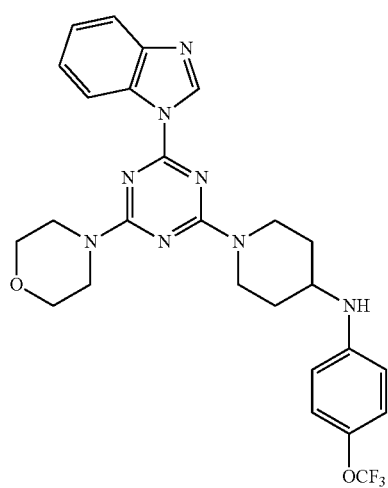 [SMILES: FC(F)(F)Oc1ccc(NC2CCN(c3nc(N4CCOCC4)nc(-n4cnc5ccccc54)n3)CC2)cc1] |
| 57 | 1B37 | 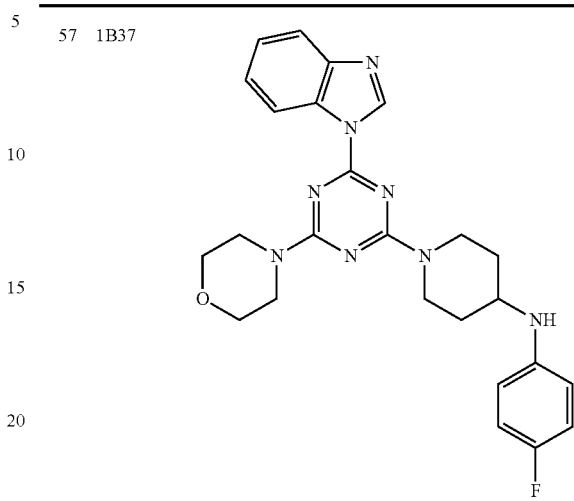 |
| 58 | 1B38 | 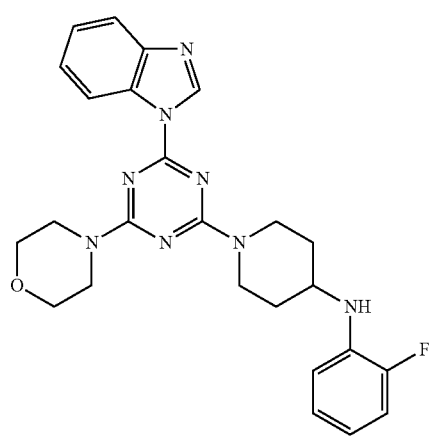 [SMILES: Fc1ccccc1NC1CCN(c2nc(N3CCOCC3)nc(-n3cnc4ccccc43)n2)CC1] |
| 59 | 1B39 | 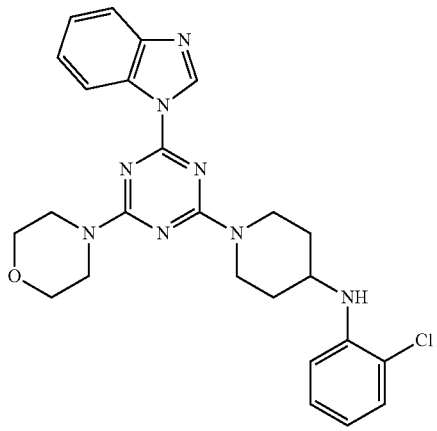 [SMILES: Clc1ccccc1NC1CCN(c2nc(N3CCOCC3)nc(-n3cnc4ccccc43)n2)CC1] |

TABLE 6-continued
| Entry | Code | Structure |
|---|---|---|
| 60 | 1B40 | 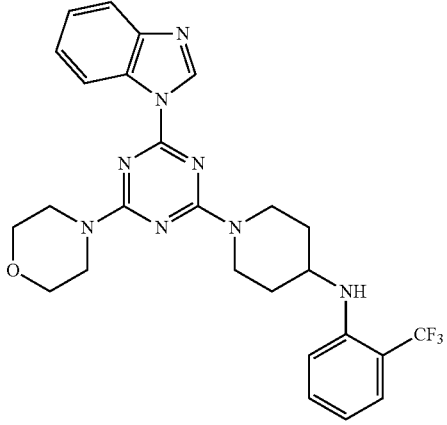 [SMILES: FC(F)(F)c1ccccc1NC1CCN(c2nc(N3CCOCC3)nc(-n3cnc4ccccc43)n2)CC1] |
TABLE 7
| Entry | Code | Structure |
|---|---|---|
| 61 | 1B41 | 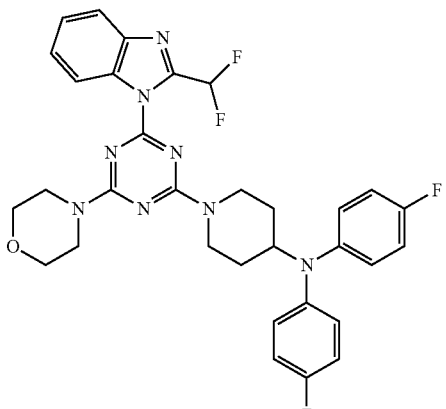 |
| 62 | 1B42 | 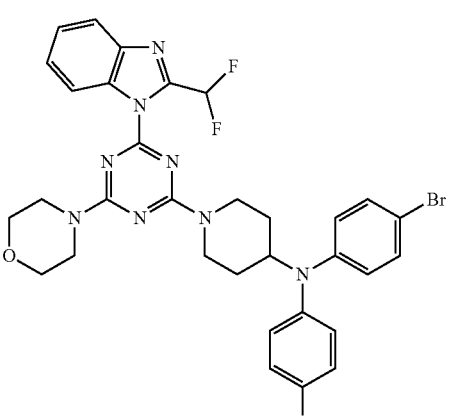 |
TABLE 7-continued
| Entry | Code | Structure |
|---|---|---|
| 63 | 1B43 | 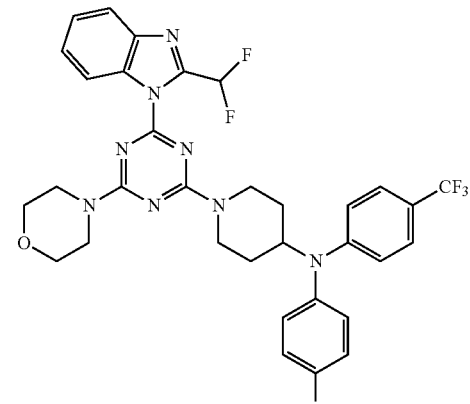 |
| 64 | 1B44 | 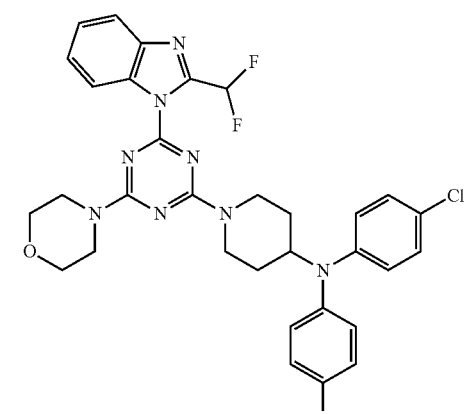 |
| 65 | 1B45 | 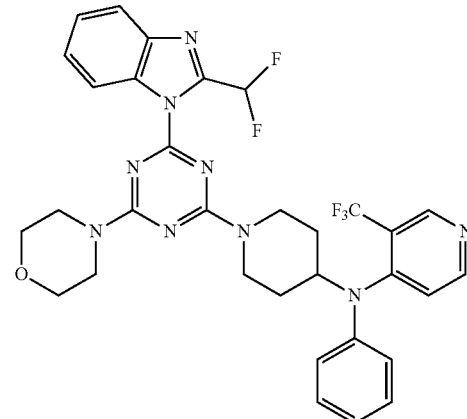 |

TABLE 7-continued

| Entry | Code | Structure |
|---|---|---|
| 66 | 1B46 | 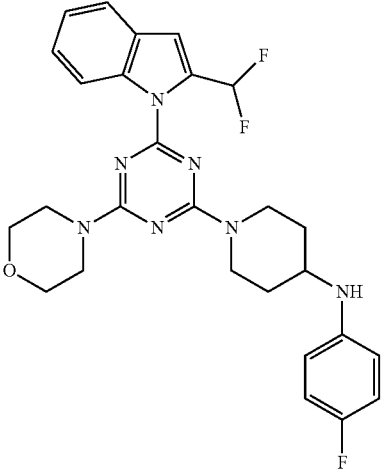 [SMILES: Fc1ccc(NC2CCN(c3nc(N4CCOCC4)nc(-n4c(C(F)F)cc5ccccc54)n3)CC2)cc1] |
| 67 | 1B47 | 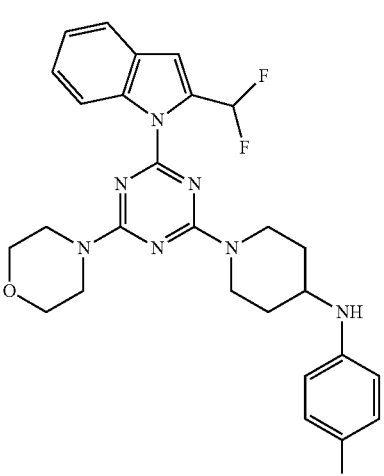 |
| 68 | 1B48 | 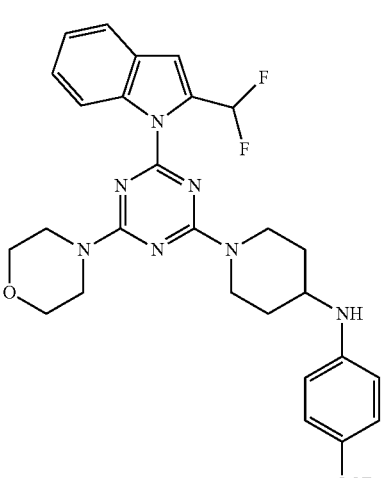 |
| 69 | 1B49 | 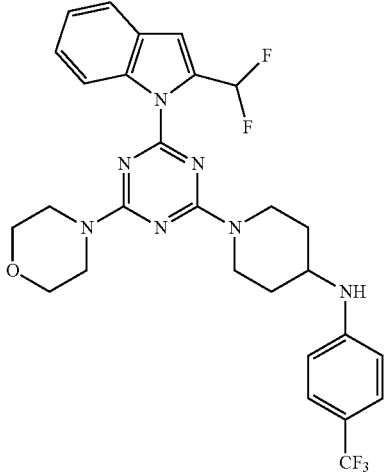 [SMILES: FC(F)c1cc2ccccc2n1-c1nc(N2CCOCC2)nc(N2CCC(Nc3ccc(C(F)(F)F)cc3)CC2)n1] |
| 70 | 1B50 | 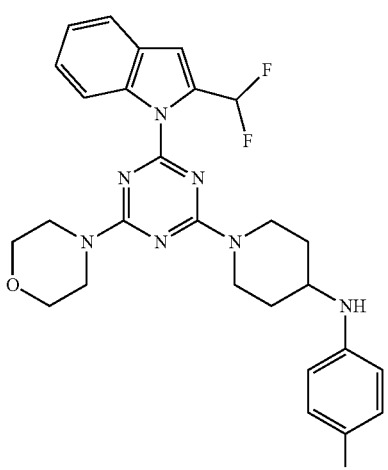 |

Part B: Biological Evaluation

Bio-Chemical Assay (PI3K Inhibition Assays).

Compounds were evaluated for their ability to inhibit class I PI3-kinase enzyme alpha as given below.

PI3K-α Assay:

PI3K alpha (diluted in 12.5 mM Glycine-NaOH (pH 8.5), 50 mM KCl, 2.5 mM MgCl$_2$, 1 mM DTT, 0.05% CHAPS) is assayed in total volume of 20 ul containing 12.5 mM glycine-NaOH (pH 8.5), 50 mM KCl, 2.5 mM MgCl$_2$, 1 mM DTT, 0.05% CHAPS, 0.01 mM ATP and 0.05 mM diC8 PIP2. The enzyme is assayed for 80 min after which 20 ul of ADP-Glo reagent is added. After a further incubation of 40 min, 40 ul of Kinase Detection Buffer is added. The assays are incubated for 40 min and then read on PerkinElmer Envision for 1 sec/well.

Results:

PI3K alpha % of inhibition values of a drug measures the effectiveness of a compound in inhibiting biological or biochemical function. The determination of enzyme based % of inhibition values helps in early analysis and estimation of the drug activities in order to narrow down drug candidates for further experimental purpose. The standard drug ZSTK474 shown greater than 70% inhibition at 500 nm against PI3K alpha and 30 compounds viz., 1A3, 1A5, 1A6, 1A8, 1A9, 1A10, 1A14, 1A15, 1A19, 1B1, 1B4, 1B8, 1B11, 1B12, IBIS, 1B18, 1B19, 1B23, 1B24, 1B25, 1B26, 1B28, 1B31, 1B34, 1B37, 1B41, 1B42, 1B43, 1B47 and 1B49 shown greater than 70% inhibition at 500 nm against PI3K alpha. All the screening results given in Table 8.

In Vitro Cell Line Activity:
Cell Culture, Growth Conditions and Treatments:

Human breast cancer cell lines MDAMB231, MFC-7 and human prostate carcinoma cell line PC-3 were obtained from European Collection of Cell Cultures (ECACC). Cells were grown in RPMI-1440 medium supplemented with 10% fetal bovine serum (FBS), penicillin (100 units/ml), streptomycin (100 μg/ml), L-glutamine (0.3 mg/ml), sodium pyruvate (550 mg/ml), and $NaHCO_3$ (2 mg/ml). Cells were grown in $CO_2$ incubator (Thermocon Electron Corporation, USA) at 37° C. in an atmosphere of 95% air and 5% $CO_2$ with 98% humidity. Different molecules were dissolved in DMSO and were delivered to cell cultures in complete medium.

Cell Proliferation Assay:

MTT assay was done to determine the viability of the cells and was done as described previously (Kumar et al, 2013). Briefly, $6 \times 10^3$ were seeded in 96 well plates and were treated with different concentrations of different molecules for 5 days. 20 μl of MTT dye (2.5 mg/ml) was added 3 h before the termination of the experiment. Formazen crystals were dissolved in 150 μl of DMSO and OD was measured at 570 nm.

Results:

The several synthesized compounds were also checked for their antiproliferative activity against two breast cancer cell lines MDAMB231, MCF-7 and one prostate cancer cell line PC-3. Many molecules displayed potent anti proliferative activities in in vitro cancer cell lines assay and all the results given in Table 9. Standard drug ZSTK474 were taken as reference standard

TABLE 8

| Entry | Code | In vitro PI3K α % of inhibition * |
|---|---|---|
| 1. | 1A1 | + |
| 2. | 1A2 | + |
| 3. | 1A3 | ++ |
| 4. | 1A4 | + |
| 5. | 1A5 | ++ |
| 6. | 1A6 | ++ |
| 7. | 1A7 | + |
| 8. | 1A8 | ++ |
| 9. | 1A9 | ++ |
| 10. | 1A10 | ++ |
| 11. | 1A11 | + |
| 12. | 1A12 | + |
| 13. | 1A13 | + |
| 14. | 1A14 | ++ |
| 15. | 1A15 | ++ |
| 16. | 1A16 | + |
| 17. | 1A17 | + |
| 18. | 1A18 | + |
| 19. | 1A19 | ++ |
| 20. | 1A20 | + |
| 21. | 1B1 | ++ |
| 22. | 1B2 | + |
| 23. | 1B3 | + |
| 24. | 1B4 | ++ |
| 25. | 1B5 | + |
| 26. | 1B6 | + |
| 27. | 1B7 | + |
| 28. | 1B8 | ++ |
| 29. | 1B9 | + |
| 30. | 1B10 | + |
| 31. | 1B11 | ++ |
| 32. | 1B12 | ++ |
| 33. | 1B13 | + |
| 34. | 1B14 | + |
| 35. | 1B15 | ++ |
| 36. | 1B16 | + |
| 37. | 1B17 | + |
| 38. | 1B18 | ++ |
| 39. | 1B19 | ++ |
| 40. | 1B20 | + |
| 41. | 1B21 | + |
| 42. | 1B22 | + |
| 43. | 1B23 | ++ |
| 44. | 1B24 | ++ |
| 45. | 1B25 | ++ |
| 46. | 1B26 | ++ |
| 47. | 1B27 | + |
| 48. | 1B28 | ++ |
| 49. | 1B29 | + |
| 50. | 1B30 | + |
| 51. | 1B31 | ++ |
| 52. | 1B32 | + |
| 53. | 1B33 | + |
| 54. | 1B34 | ++ |
| 55. | 1B35 | + |
| 56. | 1B36 | + |
| 57. | 1B37 | ++ |
| 58. | 1B38 | + |
| 59. | 1B39 | + |
| 60. | 1B40 | + |
| 61. | 1B41 | ++ |
| 62. | 1B42 | ++ |
| 63. | 1B43 | ++ |
| 64. | 1B44 | + |
| 65. | 1B45 | + |
| 66. | 1B46 | + |
| 67. | 1B47 | ++ |
| 68. | 1B48 | + |
| 69. | 1B49 | ++ |
| 70. | 1B50 | + |
| 71. | ZSTK474 | ++ |

* In vitro PI3K alpha kinase inhibition at 500 nm; + indicates greater than 50% to 70% of inhibition and ++ indicates greater than 70% of inhibition.

TABLE 9

| Entry | Code | MCF-7 Cell line % inhibition at 10 μM* | PC-3 Cell line % inhibition at 10 μM* | MDA-MB231 Cell line % inhibition at 10 μM* |
|---|---|---|---|---|
| 1. | 1A5 | + | ++ | + |
| 2. | 1A9 | ++ | + | ++ |
| 3. | 1B1 | ++ | ++ | ++ |
| 4. | 1B2 | ++ | + | ++ |
| 5. | 1B4 | NC | NC | NC |
| 6. | 1B5 | ++ | NC | + |
| 7. | 1B6 | ++ | + | NC |
| 8. | 1B7 | ++ | NC | + |
| 9. | 1B10 | NC | NC | NC |
| 10. | 1B11 | NC | ++ | + |
| 11. | 1B12 | ++ | + | + |

TABLE 9-continued

| Entry | Code | MCF-7 Cell line % inhibition at 10 μM* | PC-3 Cell line % inhibition at 10 μM* | MDA-MB231 Cell line % inhibition at 10 μM* |
|---|---|---|---|---|
| 12. | 1B22 | + | + | NC |
| 13. | 1B23 | + | + | NC |
| 14. | 1B24 | NC | NC | + |
| 15. | 1B25 | ++ | + | NC |
| 16. | 1B26 | ++ | + | ++ |
| 17. | 1B27 | ++ | + | + |
| 18. | 1B28 | ++ | + | NC |
| 19. | 1B30 | ++ | + | + |
| 20. | 1B32 | ++ | + | + |
| 21. | ZSTK474 | ++ | ++ | ++ |

*In vitro cell line inhibition at 10 μM:
+ indicates less than 30 to 50% of inhibition and
++ indicates greater than 50% of inhibition.

We claim:

1. A compound of formula 1 formula 1

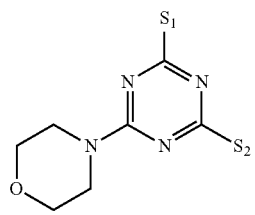

wherein substituent $S_1$ is selected from one of formula Ia or Ib

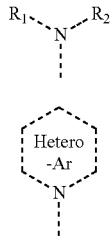

Ia

Ib and substituent $S_2$ is represented by formula Ic

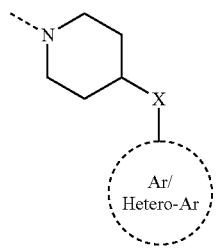

Ic wherein X is independently selected from any of $NR_3$, O, and $CH_2$, $R_1$, $R_2$ are independently selected from any of substituted or unsubstituted alkyl $C_1$-$C_{14}$, substituted or unsubstituted acyl $C_2$ to $C_{14}$, substituted or unsubstituted phenyl ring and wherein the substitution is one or more of F, Cl, Br, I, CN, $NR_4R$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl at any of the available position, $R_3$ is independently selected from any of H, substituted or unsubstituted alkyl $C_1$-$C_{14}$, substituted or unsubstituted acyl $C_2$ to $C_{14}$, substituted or unsubstituted phenyl ring and wherein the substitution is one or more of F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, cycloalkyl at any of the available position, is independently selected from any of following substituted or unsubstituted N-heterocycles selected from indolyl, triazolyl, pyrrolyl, imidazoyl, benzotriazolyl, benzoimidazolyl, and thiazoyl attached though the N-atom or through any of the available ring positions and further optionally substituted by any of F, Cl, Br, I, CN, $NR_4R_5$, $CF_3$, $CHF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, or cycloalkyl, Ar is independently selected from any of substituted or unsubstituted phenyl, substituted or unsubstituted napthyl and attached through any of the available ring position and wherein the substitution is selected from F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, and cycloalkyl, Hetero-Ar is independently selected from any of substituted or unsubstituted pyridyl, triazolyl, triazinyl, pyrimidinyl, pyridazinyl, oxazolyl, furanyl, benzofuranyl, thiophenyl, pyrrolyl, imidazoyl, thiazoyl, quinolinyl, isoquinolinyl, benzooxazolyl, and benzothiazolyl, indolyl, benzotriazolyl, and benzoimidazolyl and attached through any of the available ring position and further optionally substituted by any of F, Cl, Br, I, CN, $NR_4R_5$, $CF_3$, $CHCF_2$, $CH_2F$, $OCF_3$, $OCH_2CF_3$, $OR_6$, $NO_2$, NO, $CHR_7R_8$, alkyl chain from $C_1$ to $C_{14}$, $COOR_9$, CHO, $COR_{10}$, $COCF_3$, $COCH_2CF_3$, $SR_{11}$, $SOR_{12}$, $SO_2R_{13}$, $SONR_{14}R_{15}$, $SO_2NR_{14}R_{17}$, and cycloalkyl, $R_4$, $R_5$, $R_6$, $R_7$, $R_8$, $R_9$, $R_{10}$, $R_{11}$, $R_{12}$, $R_{13}$, $R_{14}$, $R_{15}$, $R_{14}$ and $R_{17}$ are independently selected from the group consisting of H, linear alkyl chain $C_1$-$C_{10}$, branched alkyl chain $C_3$-$C_{10}$, and substituted or unsubstituted phenyl ring.

2. The compound of claim 1, with the formula 1A or formula 1B,

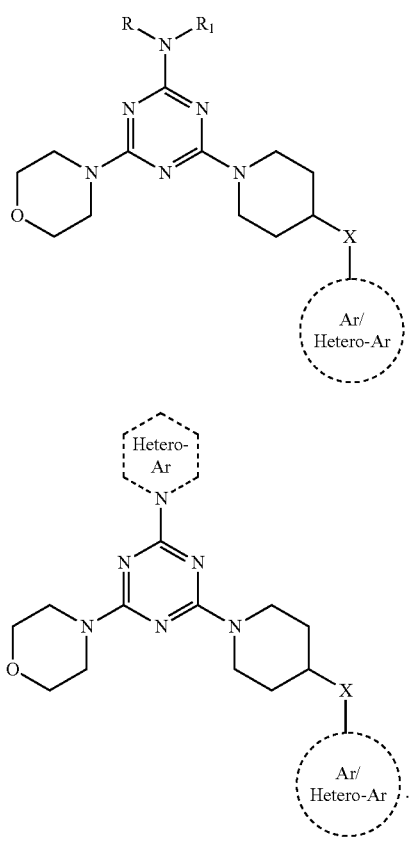

3. The compound of claim 1, wherein the compound is selected from the group consisting of:
- 4-(4-(4-fluorophenoxy)piperidin-1-yl)-N-methyl-6-morpholino-N-phenyl-1,3,5-triazin-2-amine,
- 4-(4-(2-fluorophenoxy)piperidin-1-yl)-N-methyl-6-morpholino-N-phenyl-1,3,5-triazin-2-amine,
- 4-(4-(4-fluorophenoxy)piperidin-1-yl)-N(4-fluorophenyl)-N-methyl-6-morpholino-1,3,5-triazin-2-amine,
- 2,2,2-trifluoro-N-(4-morpholino-6-(4-phenoxypiperidin-1-yl)-1,3,5-triazin-2-yl)-N-phenylacetamide,
- 2,2,2-trifluoro-N-(4-fluorophenyl)-N-(4-morpholino-6-(4-phenoxypiperidin-1-yl)-1,3,5-triazin-2-yl)acetamide,
- 2,2,2-trifluoro-N-(4-(4-(4-fluorophenoxy)piperidin-1-yl)-6-morpholino-1,3,5-triazin-2-yl)-N-(4-fluorophenyl)acetamide,
- 2,2,2-trifluoro-N-(4-morpholino-6-(4-(4-(trifluoromethoxy)phenoxy)piperidin-1-yl)-1,3,5-triazin-2-yl)-N-phenylacetamide,
- 2,2,2-trifluoro-N-(4-morpholino-6-(4-(p-tolyloxy)piperidin-1-yl)-1,3,5-triazin-2-yl)-N-phenylacetamide,
- 2,2,2-trifluoro-N-(4-morpholino-6-(4-(4-(trifluoromethoxy)phenoxy)piperidin-1-yl)-1,3,5-triazin-2-yl)-N-phenylacetamide,
- 2,2,2-trifluoro-N-(4-morpholino-6-(4-(2-(trifluoromethyl)phenoxy)piperidin-1-yl)-1,3,5-triazin-2-yl)-N-phenylacetamide,
- 2,2,2-trifluoro-N-methyl-N-(4-morpholino-6-(4-phenoxypiperidin-1-yl)-1,3,5-triazin-2-yl)acetamido,
- 2,2,2-trifluoro-N-(4-morpholino-6-(4-phenoxypiperidin-1-yl)-1,3,5-triazin-2-yl)-N-(2,2,2-trifluoroacetyl)acetamido,
- 2,2,2-trifluoro-N-(4-(4-(4-fluorophenoxy)piperidin-1-yl)-6-morpholino-1,3,5-triazin-2-yl)-N-(2,2,2-trifluoroacetyl)acetamide,
- 2,2,2-trifluoro-N-(4-(4-(2-fluorophenoxy)piperidin-1-yl)-6-morpholino-1,3,5-triazin-2-yl)-N-(2,2,2-trifluoroacetyl)acetamide,
- 2,2,2-trifluoro-N-(4-(4-(4-fluorophenoxy)piperidin-1-yl)-6-morpholino-1,3,5-triazin-2-yl)-N-methylacetamide,
- N,N-dimethyl-4-morpholino-6-(4-(p-tolyloxy)piperidin-1-yl)-1,3,5-triazin-2-amine,
- 4-(4-(4-fluorophenoxy)piperidin-1-yl)-N,N-dimethyl-6-morpholino-1,3,5-triazin-2-amine,
- 4-morpholino-6-(4-phenoxypiperidin-1-yl)-N,N-diphenyl-1,3,5-triazin-2-amine,
- 4-morpholino-N,N-diphenyl-6-(4-(2-(trifluoromethyl)phenoxy)piperidin-1-yl)-1,3,5-triazin-2-amine,
- 4-morpholino-N,N-diphenyl-6-(4-(4-(trifluoromethoxy)phenoxy)piperidin-1-yl)-1,3,5-triazin-2-amine,
- 4-(4-(2-(difluoromethyl)-1H-benzo[d]imidazol-1-yl)-6-(4-(4-fluorophenoxy)piperidin-1-yl)-1,3,5-triazin-2-yl)morpholine,
- 4-(4-(2-(difluoromethyl)-1H-benzo[d]imidazol-1-yl)-6-(4-(4-methoxyphenoxy)piperidin-1-yl)-1,3,5-triazin-2-yl)morpholine,
- 4-(4-(2-(difluoromethyl)-1H-benzo[d]imidazol-1-yl)-6-(4-(4-(trifluoromethoxy)phenoxy)piperidin-1-yl)-1,3,5-triazin-2-yl)morpholine,
- 4-(4-(2-(difluoromethyl-1H-benzo[d]imidazol-1-yl)-6-(4-(2-(trifluoromethyl)phenoxy)piperidin-1-yl)-1,3,5-triazin-2-yl)morpholine,
- 4-(4-(4-chlorophenoxy)piperidin-1-yl)-6-(2-(difluoromethyl)-1H-benzo[d]imidazol-1-yl)-1,3,5-triazin-2-yl)morpholine,
- 4-(4-(3-chlorophenoxy)piperidin-1-yl)-6-(2-(difluoromethyl)-1H-benzo[d]imidazol-1-yl)-1,3,5-triazin-2-yl)morpholine,
- 4-(4-(2-chlorophenoxy)piperidin-1-yl)-6-(2-(difluoromethyl)-1H-benzo[d]imidazol-1-yl)-1,3,5-triazin-2-yl)morpholine,
- 4-(4-(2-(difluoromethyl)-1H-benzo[d]imidazol-1-yl)-6-(4-(3-fluorophenoxy)piperidin-1-yl)-1,3,5-triazin-2-yl)morpholine,
- 4-(4-(2-(difluoromethyl)-1H-benzo[d]imidazol-1-yl)-6-(4-(2-fluorophenoxy)piperidin-1-yl)-1,3,5-triazin-2-yl)morpholine,
- 4-(4-(2-(difluoromethyl)-1H-benzo[d]imidazol-1-yl)-6-(4-(p-tolyloxy)piperidin-1-yl)-1,3,5-triazin-2-yl)morpholino,
- 4-(4-(2-(difluoromethyl)-1H-benzo[d]imidazol-1-yl)-6-(4-(m-tolyloxy)piperidin-1-yl)-1,3,5-triazin-2-yl)morpholine,
- 4-(4-(2-(difluoromethyl)-1H-benzo[d]imidazol 1-yl)-6-(4-(o-tolyloxy)piperidin-1-yl)-1,3,5-triazin-2-yl)morpholine, 4-(4-(5-fluoro-1H-benzo[d]imidazol-1-yl)-6-(4-(p-toly-loxy)piperidin-1-yl)-1,3,5-triazin-2-yl)morpholine, 4-(4-(5-fluoro-1H-benzo[d]imidazol-1-yl)-6-(4-(4-(trifluoromethyl)phenoxy)piperidin-1-yl)-1,3,5-triazin-2-yl)morpholine, 4-(4-(1H-benzo[d]imidazol-1-yl)-6-(4-(4-(trifluoromethyl)phenoxy)piperidin-1-yl)-1,3,5-triazin-2-yl)morpholine, 4-(4-(1H-benzo[d]imidazol-1-yl)-6-(4-(4-(trifluoromethoxy)phenoxy)piperidin-1-yl)-1,3,5-triazin-2-yl)morpholine, 4-(4-(1H-benzo[d]imidazol-1-yl)-6-(4-(4-fluorophenoxy)piperidin-1-yl)-1,3,5-triazin-2-yl)morpholine, 4-(4-(1H-benzo[d]imidazol-1-yl)-6-(4-(2-fluorophenoxy)piperidin-1-yl)-1,3,5-triazin-2-yl)morpholine, 4-(4-(1H-benzo[d]imidazol-1-yl)-6-(4-(2-chlorophenoxy)piperidin-1-yl)-1,3,5-triazin-2-yl)morpholine, 4-(4-(1H-benzo[d]imidazole-1-yl)-6-(4-(2-(trifluoromethyl)phenoxy)piperidin-1-yl)-1,3,5-triazin-2-yl)morpholine, 1-(4-(2-(difluoromethyl)-1H-benzo[d]imidazol-1-yl)-6-morpholino-1,3,5-triazin-2-yl)-N-(4-fluorophenyl)piperidin-4-amine, 1-(4-(2-(difluoromethyl)-1H-benzo[d]imidazol-1-yl)-6-morpholino-1,3,5-triazin-2-yl)-N-(4-(trifluoromethyl)phenyl)piperidin-4-amine, 1-(4-(2-(difluoromethyl)-1H-benzo[d]imidazol 1-yl)-6-morpholino-1,3,5-triazin-2-yl)-N-(4-(trifluoromethoxy)phenyl)piperidin-4-amine, 1-(4-(2-(difluoromethyl)-1H-benzo[d]imidazole 1-yl)-6-morpholino-1,3,5-triazin-2-yl)-N-(4-methoxyphenyl)piperidin-4-amine, N-(4-bromophenyl)-1-(4-(2-(difluoromethy-1H-benzo[d]imidazol-1-yl)-6-morpholino-1,3,5-triazin-2-yl)piperidin-4-amine, N-(3,4-dichlorophenyl)-1-(4-(2-(difluoromethyl)-1H-benzo[d]imidazol-1-yl)-6-morpholino-1,3,5-triazin-2-yl)piperidin-4-amine, 1-(4-(2-(difluoromethyl)-1H-benzo[d]imidazol-1-yl)-6-morpholino-1,3,5-triazin-2-yl)-N-(2-fluorophenyl)piperidin-4-amine, 1-(4-(2-(difluoromethyl)-1H-benzo[d]imidazol-1-yl)-6-morpholino-1,3,5-triazin-2-yl)-N-(2-methoxyphenyl)piperidin-4-amine, 1-(4-(2-(difluoromethyl)-1H-benzo[d]imidazol-1-yl)-6-morpholino-1,3,5-triazin-2-yl)-N-(2-(trifluoromethyl)phenyl)piperidin-4-amine, 1-(4-(2-(difluoromethy)-1H-benzo[d]imidazol-1-yl)-6-morpholino-1,3,5-triazin-2-yl)-N-(p-tolyl)piperidin-4-amine, 1-(4-(2-(difluoromethyl)-1H-benzo[d]imidazol-1-yl)-6-morpholino-1,3,5-triazin-2-yl)-N-(3-methoxyphenyl)piperidin-4-amine, 1-(4-(2-(difluoromethyl)-1H-benzo[d]imidazol-1-yl)-6-morpholino-1,3,5-triazin-2-yl)-N-(o-tolyl)piperidin-4-amine, 1-(4-(2-(difluoromethyl)-5-fluoro-1H-benzo[d]imidazol-1-yl)-6-morpholino-1,3,5-triazin-2-yl)-N-(p-tolyl)piperidin-4-amine, 1-(4-(2-(difluoromethyl)-5-fluoro-1H-benzo[d]imidazol-1-yl)-6-morpholino-1,3,5-triazin-2-yl)-N-(4-(trifluoromethyl)phenyl)piperidin-4-amine, 1-(4-(2-(difluoromethyl)-1H-benzo[d]imidazol-1-yl)-6-morpholino-1,3,5-triazin-2-yl)-N-(4-(trifluoromethyl)phenyl)piperidin-4-amine, 1-(4-(2-(difluoromethyl)-1H-benzo[d]imidazol-1-yl)-6-morpholino-1,3,5-triazin-2-yl)-N-(4-(trifluoromethoxy)phenyl)piperidin-4-amine, 1-(4-(2-(difluoromethyl)-1H-benzo[d]imidazol-1-yl)-6-morpholino-1,3,5-triazin-2-yl)-N-(4-fluorophenyl)piperidin-4-amine, 1-(4-(2-(difluoromethyl)-1H-benzo[d]imidazol-1-yl)-6-morpholino-1,3,5-triazin-2-yl)-N-(2-fluorophenyl)piperidin-4-amine, N-(2-chlorophenyl)-1-(4-(2-(difluoromethyl)-1H-benzo[d]imidazol-1-yl)-6-morpholino-1,3,5-triazin-2-yl)piperidin-4-amine, 1-(4-(2-(difluoromethyl)-1H-benzo[d]imidazol-1-yl)-6-morpholino-1,3,5-triazin-2-yl)-N-(2-(trifluoromethyl)phenyl)piperidin-4-amine, 1-(4-(2-(difluoromethyl)-1H-benzo[d]imidazol-1-yl)-6-morpholino-1,3,5-triazin-2-yl)-N,N-bis(4-fluorophenyl)piperidin-4-amine, N-(4-bromophenyl)-1-(4-(2-(difluoromethyl)-1H-benzo[d]imidazol-1-yl)-6-morpholino-1,3,5-triazin-2-yl)-N-(4-fluorophenyl)piperidin-4-amine, 1-(4-(2-(difluoromethyl)-1H-benzo[d]imidazol-1-yl)-6-morpholino-1,3,5-triazin-2-yl)-N-(4-fluorophenyl)-N-(4-(trifluoromethyl)phenyl)piperidin-4-amine, N-(4-chlorophenyl)-1-(4-(2-(difluoromethyl)-1H-benzo[d]imidazol-1-yl)-6-morpholino-1,3,5-triazin-2-yl)-N-(4-fluorophenyl)piperidin-4-amine, N-(1-(4-(2-(difluoromethyl)-1H-benzo[d]imidazol-1-yl)-6-morpholino-1,3,5-triazin-2-yl)piperidin-4-yl)-N-(4-fluorophenyl)-3-(trifluoromethyl)pyridin-4-amine, 1-(4-(2-(difluoromethyl)-1H-indol-1-yl)-6-morpholino-1,3,5-triazin-2-yl)-N-(4-fluorophenyl)piperidin-4-amine, 1-(4-(2-(difluoromethyl)-1H-indol-1-yl)-6-morpholino-1,3,5-triazin-2-yl)-N(4-methoxyphenyl)piperidin-4-amine, 1-(4-(2-(difluoromethyl)-1H-indol-1-yl)-6-morpholino-1,3,5-triazin-2-yl)-N-(4-(trifluoromethoxy)phenyl)piperidin-4-amine, 1-(4-(2-(difluoromethyl)-1H-indol-1-yl)-6-morpholino-1,3,5-triazin-2-yl)-N-(4-(trifluoromethyl)phenyl)piperidin-4-amine, and N-(4-chlorophenyl)-1-(4-(2-(difluoromethyl)-1H indol-1-yl)-6-morpholino-1,3,5-triazin-2-yl)piperidin-4-amine.

4. A method of inhibiting PI3K kinase comprising contacting the kinase with a compound of claim 1.

5. A method of treating cancer comprising administering the compound of claim 1 to a patient in need thereof.

6. A process for the preparation of the compound of claim 1, comprising:

(i) reacting a compound of formula 5 or 8,

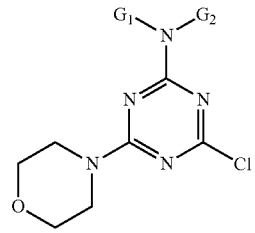

formula 5

-continued formula 8
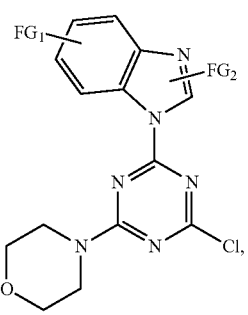

with
an aryloxy piperidine of formula 6 or a piperidone of formula 9 formula 6
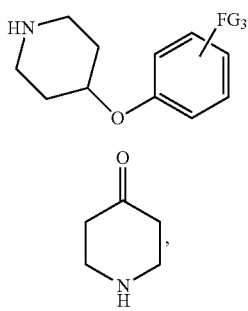

formula 9
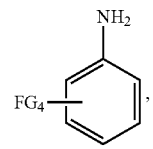

in an organic solvent selected from the group consisting of DMF, THF, and CH₃CN (added) in the presence of alkali metal carbonate selected from the group consisting of K₂CO₃, Na₂CO₃, and Cs₂CO₃ at a temperature ranging between 10° C. to 80° C. for a period ranging between 1 to 24 hrs, to obtain compound of formula 1 or a compound of formula 10 or formula 15, formula 10
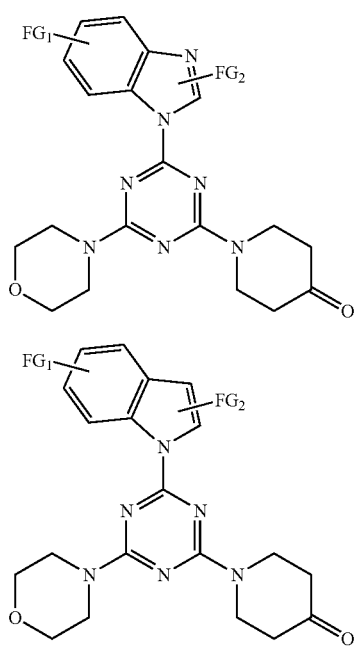

formula 15

(ii) reacting a compound of formula 10 or formula 15, with a substituted aryl amine of formula 11, formula 11
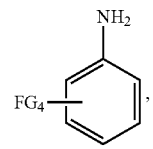

in an organic solvent selected from a group consisting of DCM, DCE, THF, MeOH in presence of acetic acid and a reducing agent selected from a group consisting of sodium triacetoxy borohydride and sodium borohydride at a temperature ranging between 10° C. to 80° C. for a period ranging between 1 to 24 hrs, to obtain compound of formula 1, (iii) reacting a compound of formula 1B21, formula 1B21
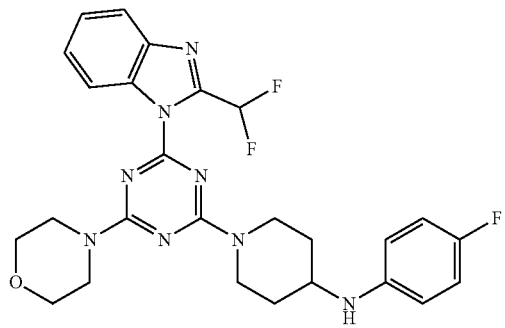

with a substituted aryl boronic acid of formula 12, formula 12
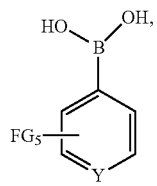

in an organic solvent selected from the group consisting of DCM, DCE, MeOH, and CH₃CN in the presence of triethylamine and copper acetate, at a temperature ranging between 10° C. to 80° C. for a period in the range of 1 to 24 hrs, to obtain compound of formula 1, wherein
$G_1$ is selected from the group consisting of Ph, (4-F)-Ph, CH₃, and COCF₃;
$G_2$ is selected from the group consisting of CH₃, COCF₃ and Ph;
$FG_1$ is H or F;
$FG_2$ is 2-CHF₂ or H;
$FG_3$ is selected from the group consisting of 4-F, 4-OMe, 2-CF₃, 4-Cl, 3-Cl, 2-Cl, 4-CN, 2-CN, 4-CH₃, 3-CH₃, 2-CH₃, 4-CF₃, 4-OCF₃, 4-F, 2-F, 4-Cl, 2-CF₃;
$FG_4$ is selected from the group consisting of 4-F, 4-CF₃, 4-OCH₃, 4-Br, 3, 4-di-Cl, 2-F, 2-OCH₃, 2-CF₃, 3-OCH₃, 2-CH₃, 4-CH₃, 4-OCF₃, 4-Cl;

FG$_5$ is halogen or CF$_3$; and

Y is CH or N.

7. The process of claim 6, wherein the aryloxy piperidine is selected from the group consisting of 4-(4-fluorophenoxy)piperidine, 4-(4-methoxy phenoxy)piperidine, 4-(4-(trifluoromethoxy phenoxy)piperidine, 4-(2-(trifluoromethyl)phenoxy)piperidine, 4-(4-chlorophenoxy)piperidine, 4-(3-chloro phenoxy)piperidine, 4-(2-chlorophenoxy)piperidine, 4-(p-tolyloxy)piperidine, 4-(m-tolyloxy)piperidine, 4-(o-tolyloxy)piperidine, 4-(4-(trifluoromethyl)phenoxy)piperidine, 4-(piperidin-4-yloxy)benzonitrile, 2-(piperidin-4-yloxy)benzonitrile, and 4-(2-fluorophenoxy)piperidine.

8. The process claim 6, wherein the substituted aryl amine is selected from the group consisting of 4-Fluoro aniline, 4-Trifluoromethylaniline, 4-Trifluoromethoxy aniline, 4-Methoxy aniline, 4-Bromo aniline, 3, 4-Dichloro aniline, 2-Fluoro aniline, 2-Methoxy aniline, 2-Trifluoromethylaniline, 3-Methoxy aniline, 2-Methylaniline, 3 Methylaniline, and 4-Methylaniline.

* * * * *